US010640541B2

(12) United States Patent
You et al.

(10) Patent No.: US 10,640,541 B2
(45) Date of Patent: May 5, 2020

(54) METHOD FOR PREPARING COMPOSITION FOR PROMOTING HAIR GROWTH USING NANOG-INTRODUCED MESENCHYMAL STEM CELLS DERIVED FROM FETUS IN AMNIOTIC FLUID

(71) Applicant: Stemlab Inc., Seoul (KR)

(72) Inventors: Seung Kwon You, Yongin-si (KR); Eun Kyoung Jun, Chungcheongnam-do (KR); Jung Hyun Park, Seoul (KR); Won-Jin Yun, Gyeonggi-do (KR); Da-Ryeon Son, Gyeongsangnam-do (KR)

(73) Assignee: Stemlab Inc., Seoul (KR)

( * ) Notice: Subject to any disclaimer, the term of this patent is extended or adjusted under 35 U.S.C. 154(b) by 148 days.

(21) Appl. No.: 15/760,280

(22) PCT Filed: Sep. 9, 2016

(86) PCT No.: PCT/KR2016/010177
§ 371 (c)(1),
(2) Date: Mar. 15, 2018

(87) PCT Pub. No.: WO2017/047996
PCT Pub. Date: Mar. 23, 2017

(65) Prior Publication Data
US 2018/0362606 A1 Dec. 20, 2018

(30) Foreign Application Priority Data

Sep. 15, 2015 (KR) .................. 10-2015-0130125

(51) Int. Cl.
C07K 14/50 (2006.01)
C07K 14/49 (2006.01)
C07K 14/65 (2006.01)
A61K 8/98 (2006.01)
C07K 14/475 (2006.01)
A61K 35/50 (2015.01)
A61P 17/14 (2006.01)
A61K 8/64 (2006.01)
A61K 38/17 (2006.01)
A61K 38/18 (2006.01)
A61K 38/30 (2006.01)
A61Q 7/00 (2006.01)
C07K 14/47 (2006.01)

(52) U.S. Cl.
CPC .............. C07K 14/503 (2013.01); A61K 8/64 (2013.01); A61K 8/98 (2013.01); A61K 35/50 (2013.01); A61K 38/1709 (2013.01); A61K 38/1825 (2013.01); A61K 38/1858 (2013.01); A61K 38/30 (2013.01); A61P 17/14 (2018.01); A61Q 7/00 (2013.01); C07K 14/47 (2013.01); C07K 14/475 (2013.01); C07K 14/49 (2013.01); C07K 14/50 (2013.01); C07K 14/65 (2013.01)

(58) Field of Classification Search
CPC .... C07K 14/50; C07K 14/503; C07K 14/475; C07K 14/47; C07K 14/65; C07K 14/49; A61K 35/50; A61K 8/98; A61K 38/30; A61K 38/1858; A61K 38/1825; A61K 38/1709; A61K 8/64; A61P 17/14; A61Q 7/00
See application file for complete search history.

(56) References Cited

U.S. PATENT DOCUMENTS

2012/0141399 A1  6/2012  You et al.

FOREIGN PATENT DOCUMENTS

| JP | 2009-011254 | 1/2009 | |
| JP | 2015-077074 | 4/2015 | |
| JP | 2015-526067 | 9/2015 | |
| KR | 10-2010-0105167 | 9/2010 | |
| KR | 10-2012-0008223 | 1/2012 | |
| KR | 10-2013-0003159 | 1/2013 | |
| KR | 10-2014-0057437 | 5/2014 | |
| KR | 10-2014-0125735 | 10/2014 | |
| WO | WO-2009005155 A1 * | 1/2009 | ......... G01N 33/5073 |
| WO | WO 2010/107287 | 9/2010 | |
| WO | WO 2014/003319 | 1/2014 | |

OTHER PUBLICATIONS

Go et al., Exp Cell Res. Mar. 10, 2008;314(5):1147-1154 (Year: 2008).*
Notice of Reasons for Rejection dated Mar. 4, 2019 From the Japan Patent Office Re. Application No. 2018-513880. (6 Pages).
Supplementary European Search Report and the European Search Opinion dated Feb. 20, 2019 From the European Patent Office Re. Application No. 16846817.1. (8 Pages).
Son et al. "Magnetofection Mediated Transient NANOG Overexpression Enhances Proliferation and Myogenic Differentiation of Human Hair Follicle Derived Mesenchymal Stem Cells", Bioconjugate Chemistry, XP055547108, 26(7): 1314-1327, Published Online Mar. 10, 2015.

(Continued)

Primary Examiner — Daniel C Gamett

(57) ABSTRACT

The present invention relates to a culture solution of MSCs derived from a fetus in amniotic fluid, and more specifically, to a composition for promoting hair growth or preventing hair loss, which includes a culture solution of MSCs overexpressing a reprogramming factor Nanog and derived from a fetus in amniotic fluid as an active ingredient. In addition, the present invention relates to a method for preparing the composition, which includes culturing Nanog-introduced MSCs derived from a fetus in amniotic fluid in a conditioned medium and collecting the culture solution. The conditioned medium composition according to the present invention exhibits a hair growth promoting effect, and thus is able to be used as cosmetic and pharmaceutical compositions for promoting hair growth.

7 Claims, 12 Drawing Sheets
Specification includes a Sequence Listing.

(56) References Cited

OTHER PUBLICATIONS

Ullah et al. "Human Mesenchymal Stem Cells—Current Trends and Future Prospective", Bioscience Reports, XP055532896, 35(2): e00191-1-e00191-18, Published Online Mar. 23, 2015.

Walter et al. "Mesenchymal Stem Cell-Conditioned Medium Accelerates Skin Wound Healing: An in Vitro Study of Fibroblast and Keratinocyte Scratch Assays", Experimental Cell Research, XP055192472, 316(7): 1271-1281, Available Online Mar. 3, 2010.

Yoon et al. "Secretory Profiles and Wound Healing Effects of Human Amniotic Fluid-Derived Mesenchymal Stem Cells", Stem Cells and Development, XP002788296, 19(6): 887-902, Jun. 2010.

Liu et al. "Effects of Ectopic Nanog and Oct4 Overexpression on Mesenchymal Stem Cells", Stem Cells and Development, 18(7): 1013-1022, Sep. 2009.

Yamahara et al. "Comparison of Angiogenic, Cytoprotective, and Immunosuppressive Properties of Human Amnion- and Chorion-Derived Mesenchymal Stem Cells", PLOS One, 9(2): e88319-1-e88319-7, Feb. 14, 2014.

International Search Report dated Dec. 21, 2016 From the Korean Intellectual Property Office Re. Application No. PCT/KR2016/010177. (2 Pages).

\* cited by examiner

[Fig. 1]
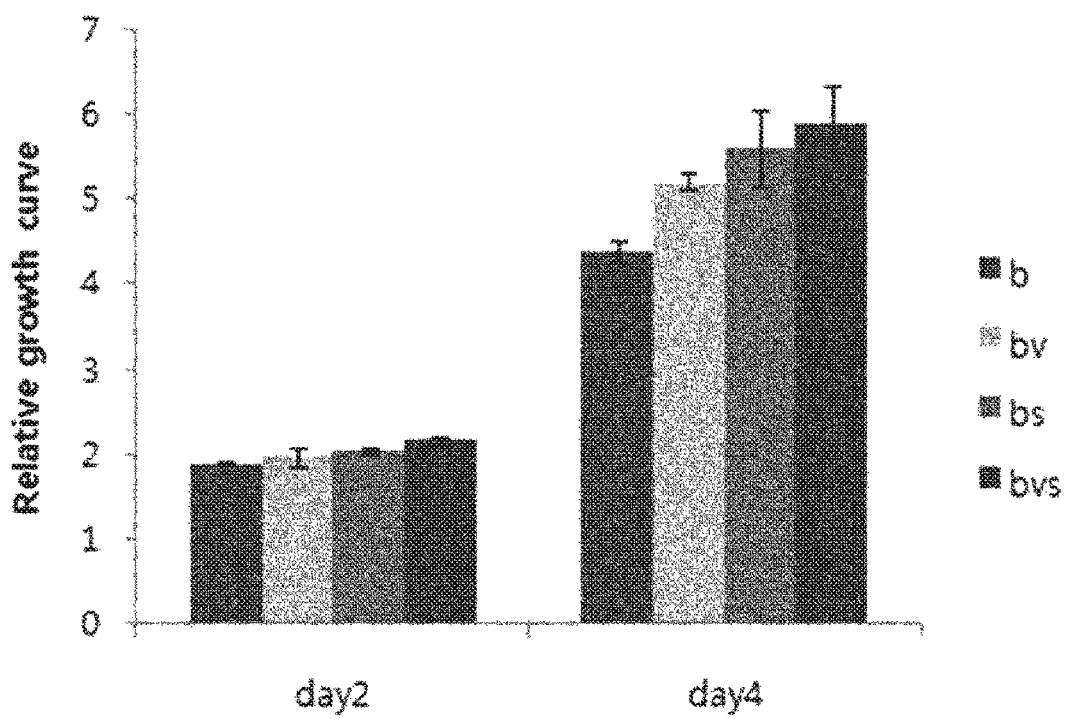
[Fig. 2]
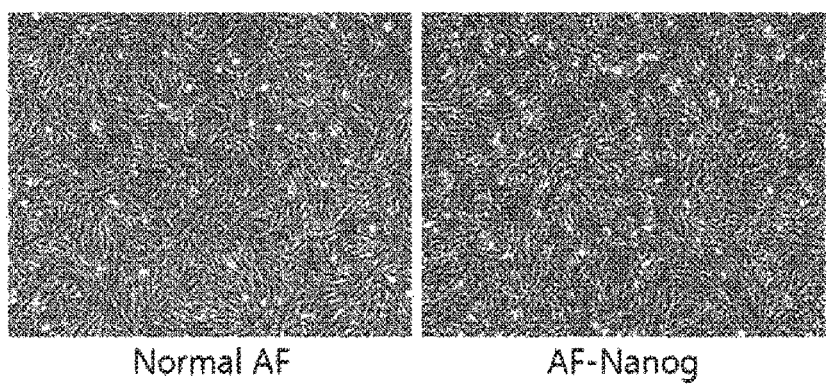

[Fig. 3]
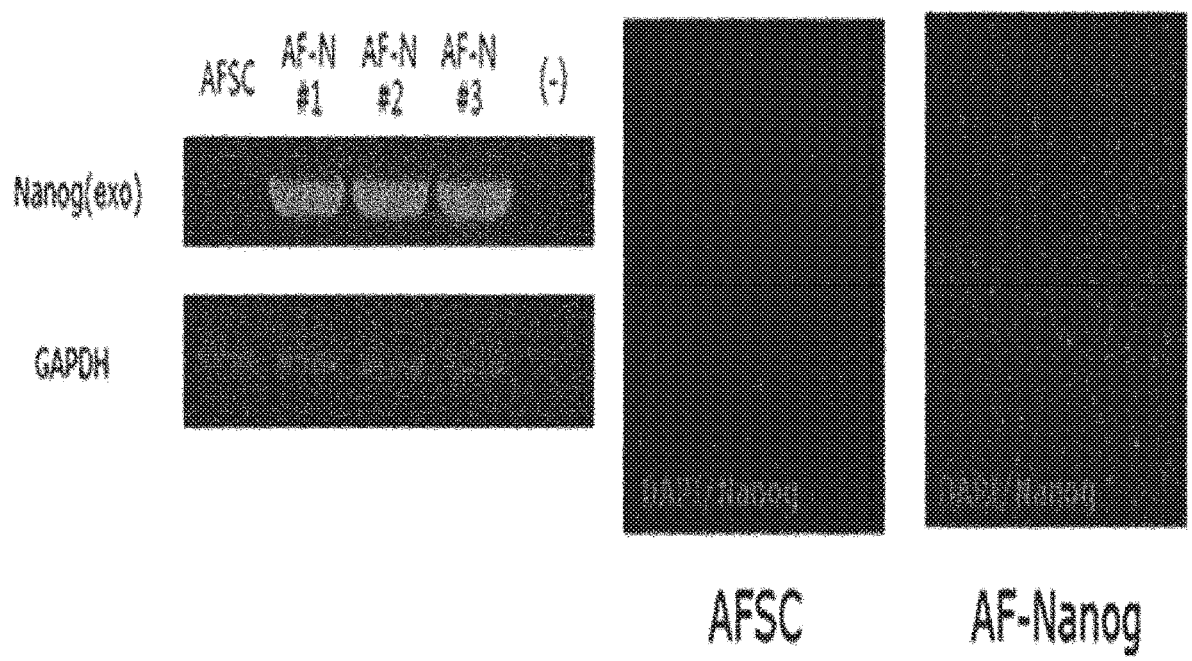

[Fig. 4]
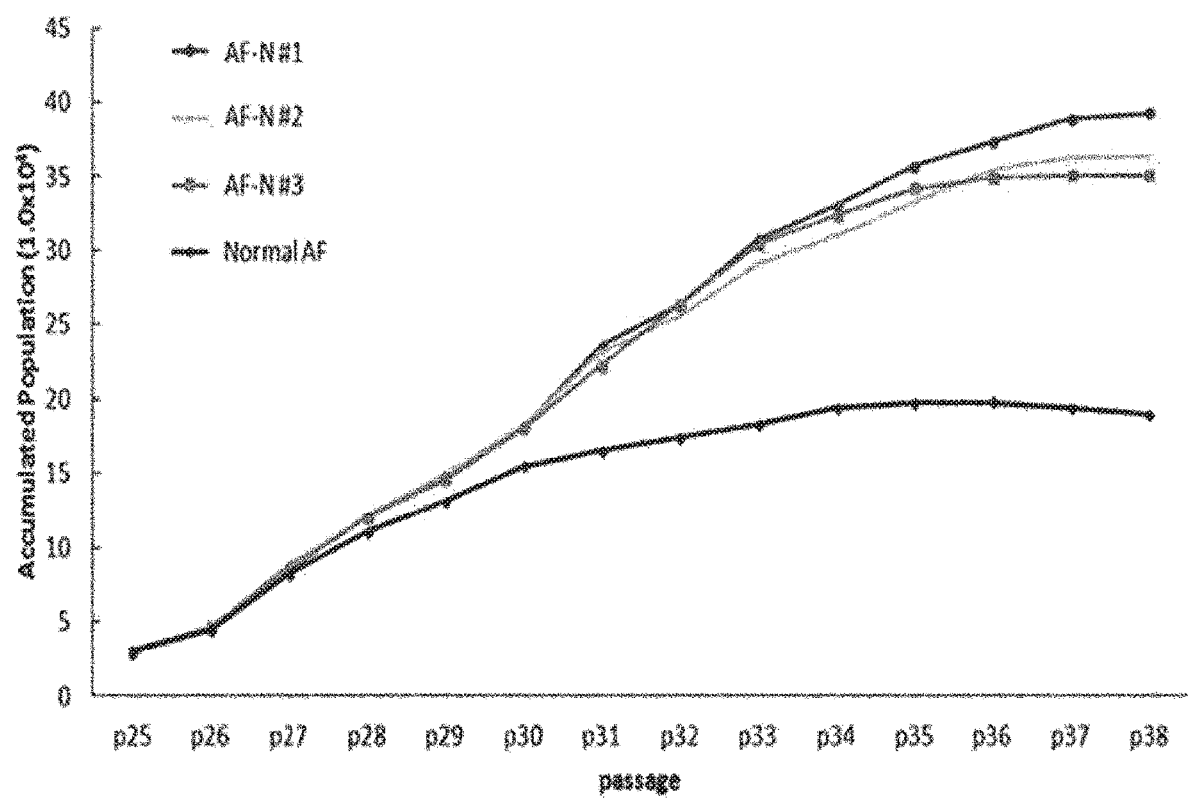

[Fig. 5]
β-gal staining (p35)
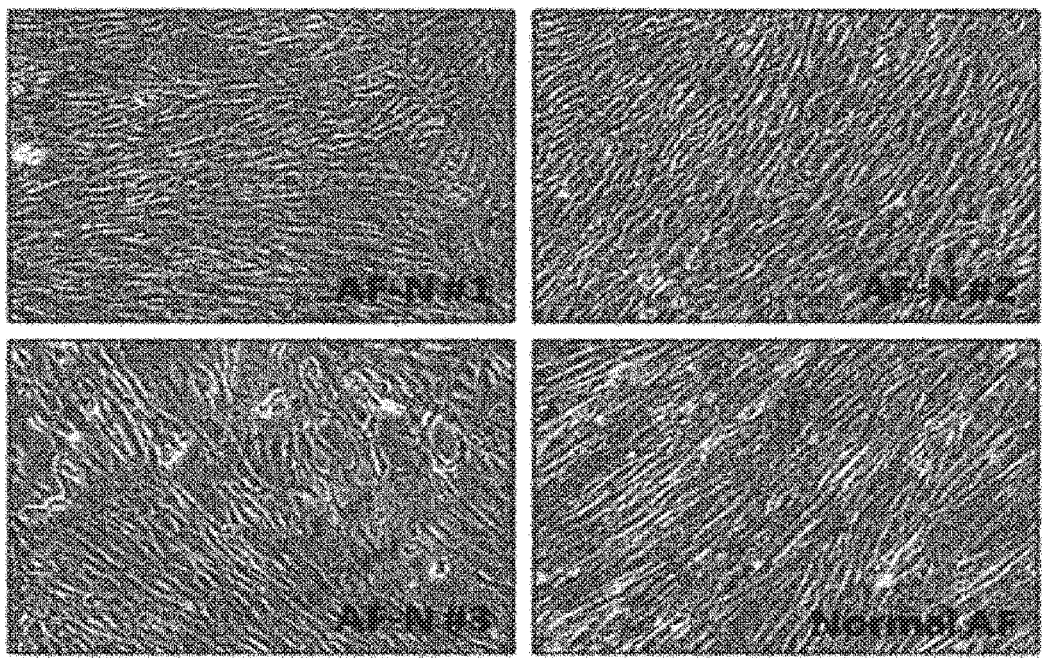
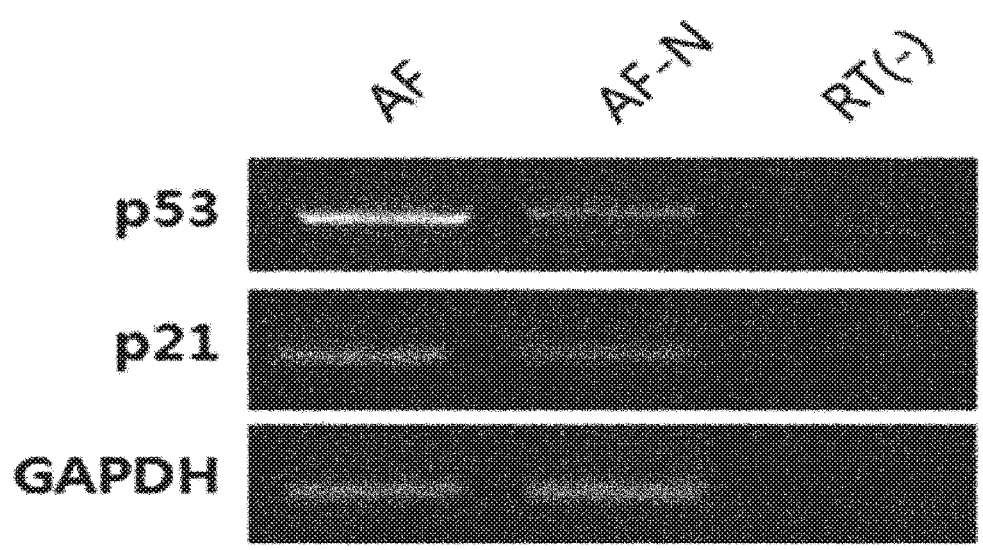

[Fig. 6]
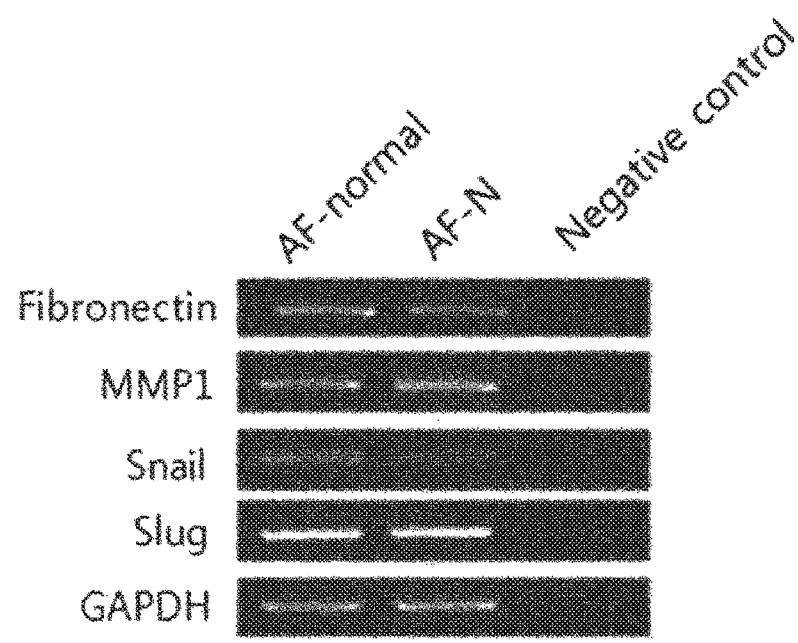
[Fig. 7]
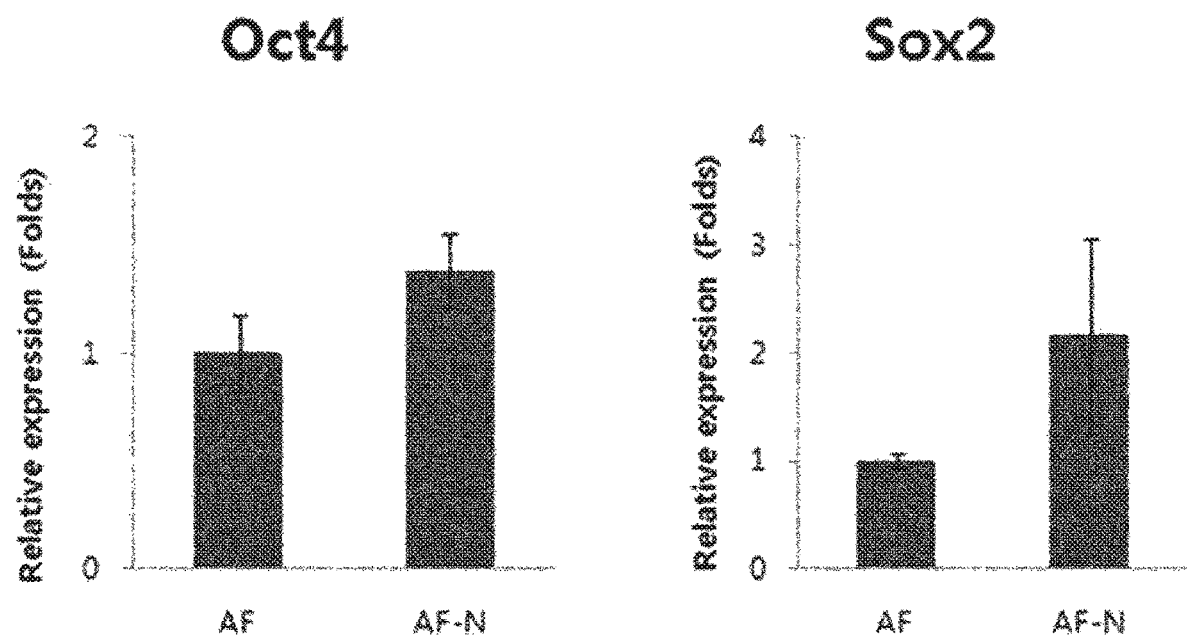

[Fig. 8]
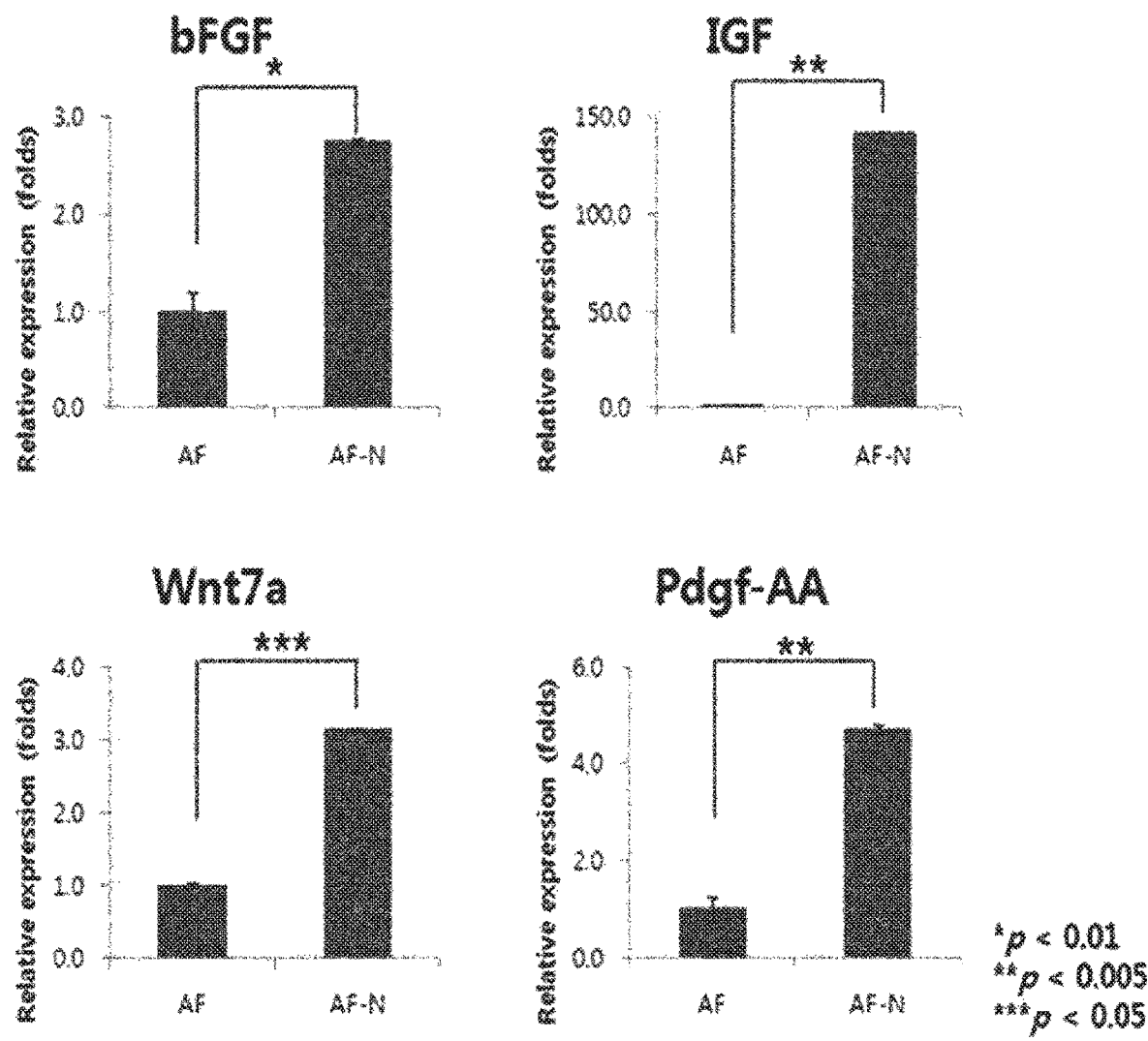

[Fig. 9]
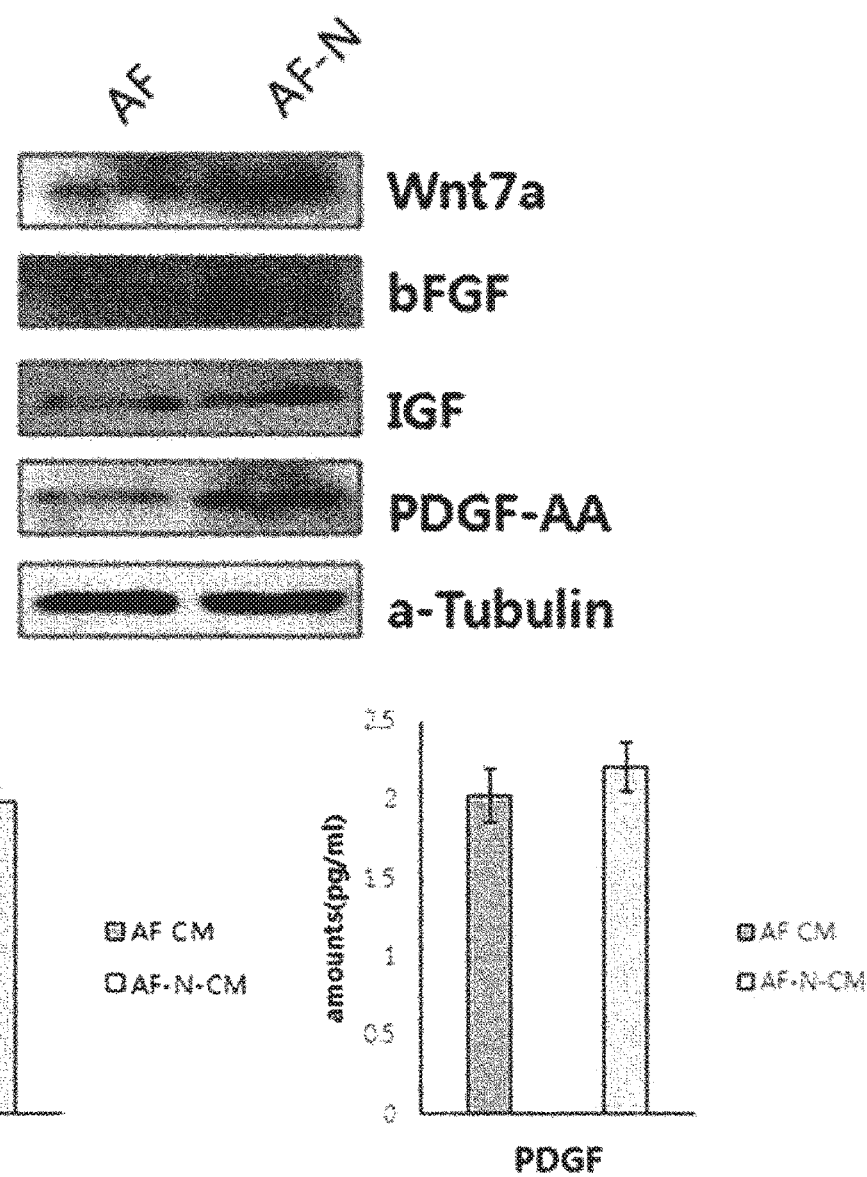

[Fig. 10]
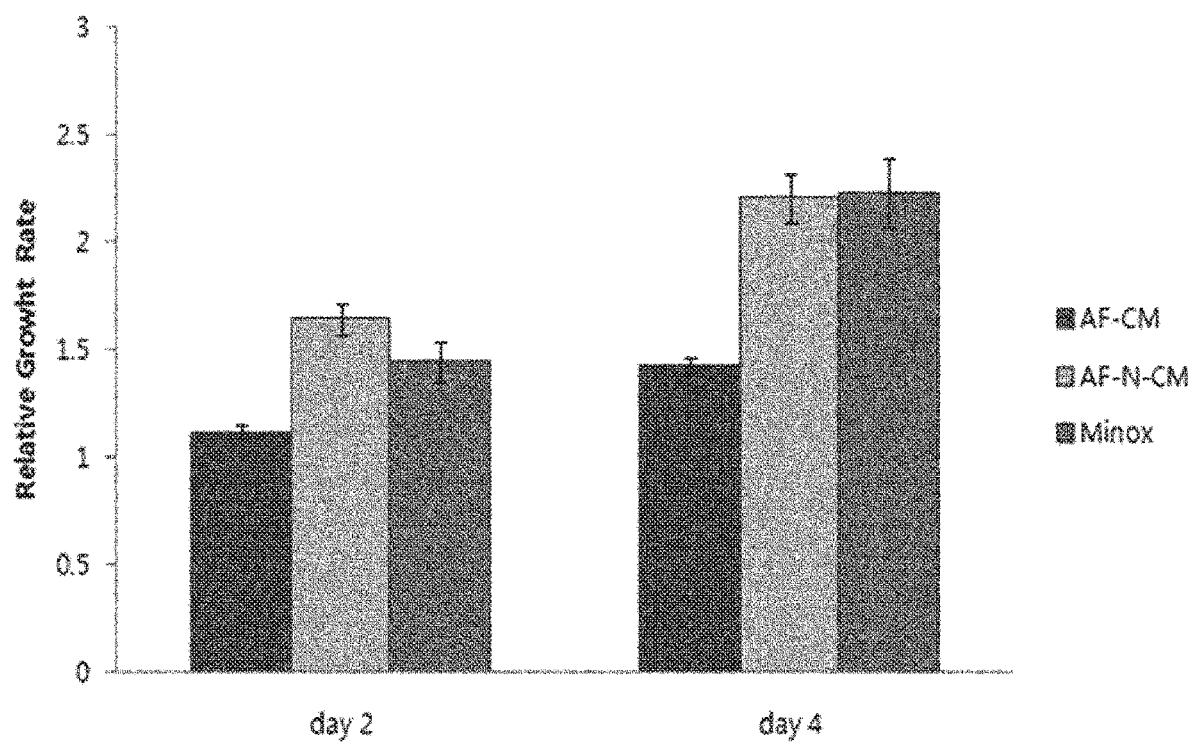

[Fig. 11]
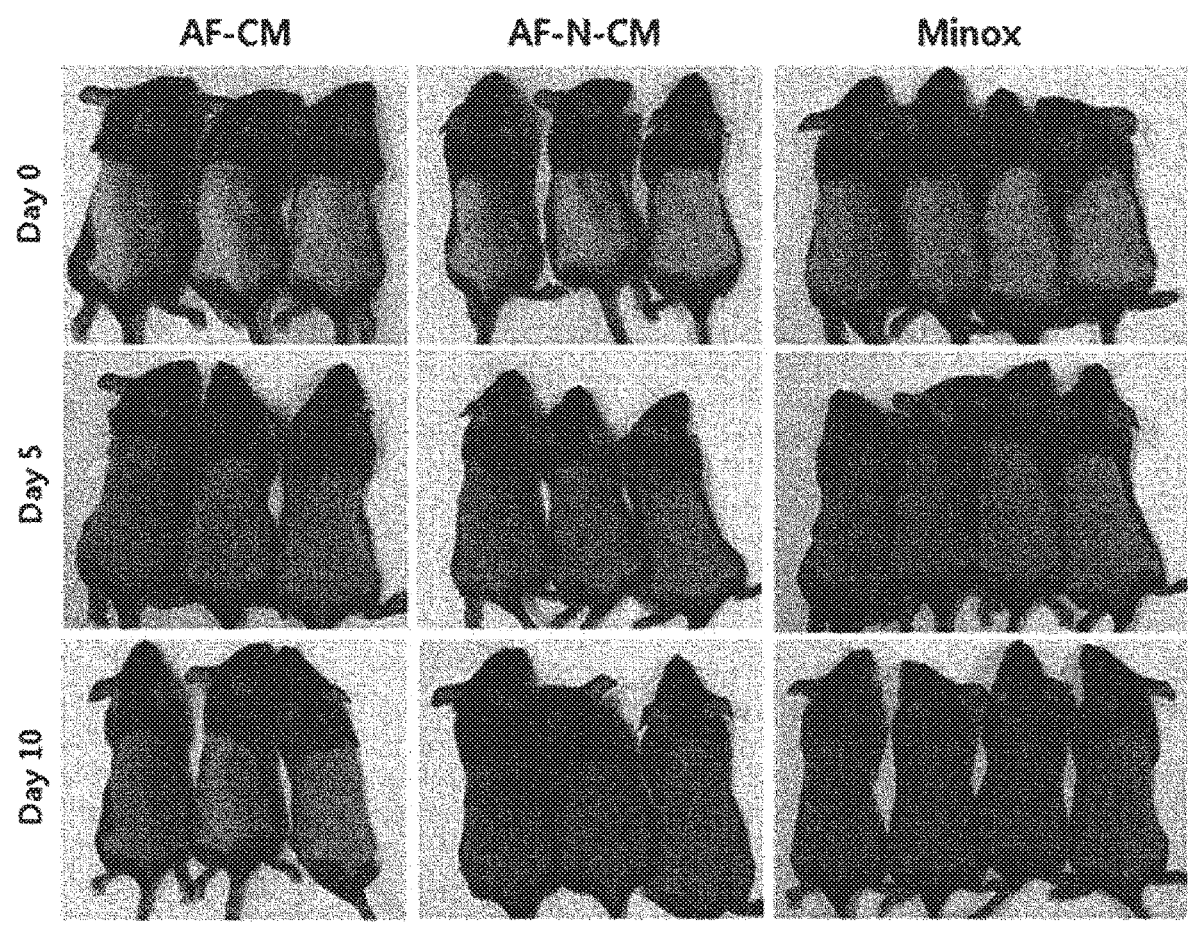

[Fig. 12]
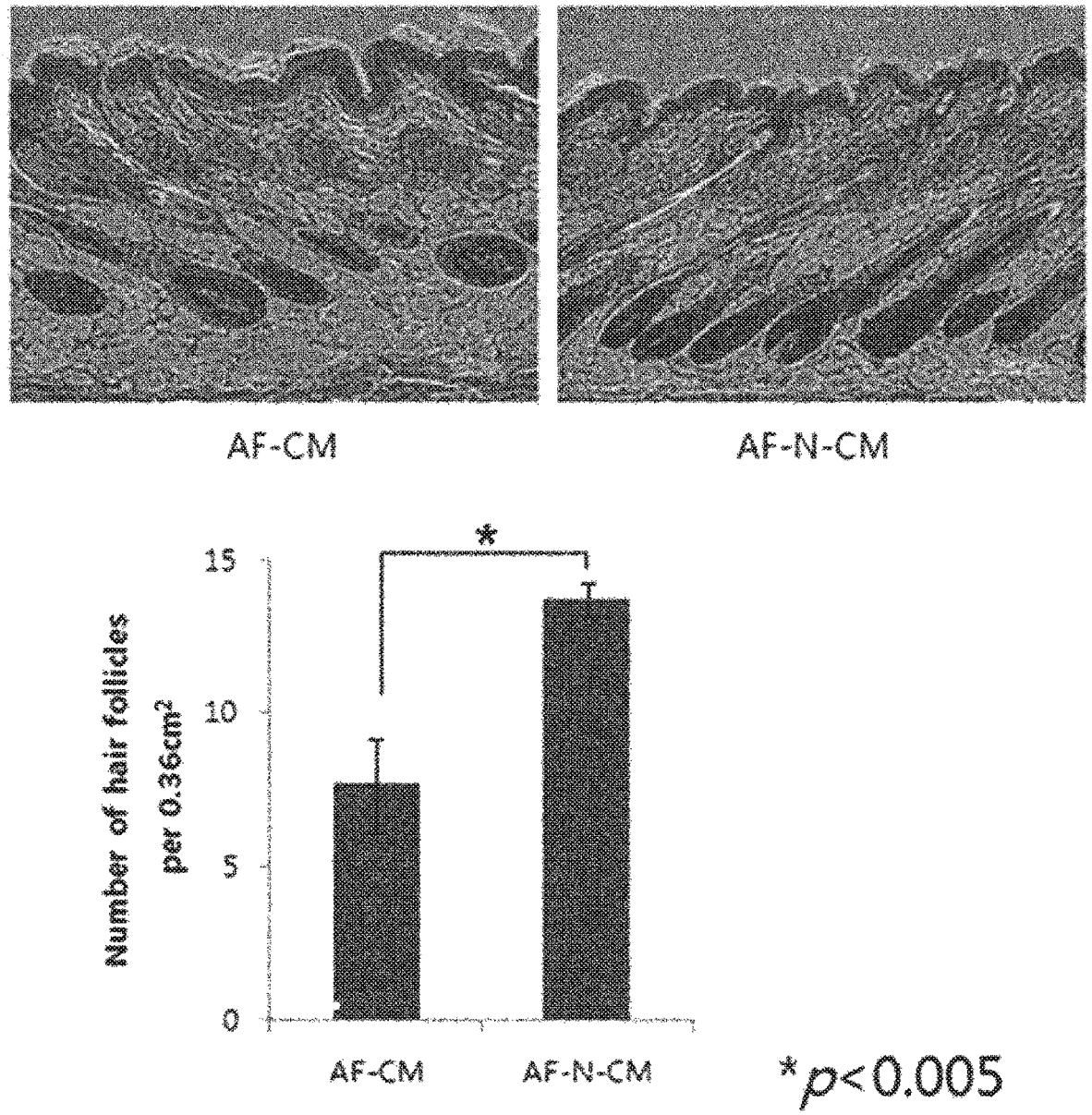

[Fig. 13]
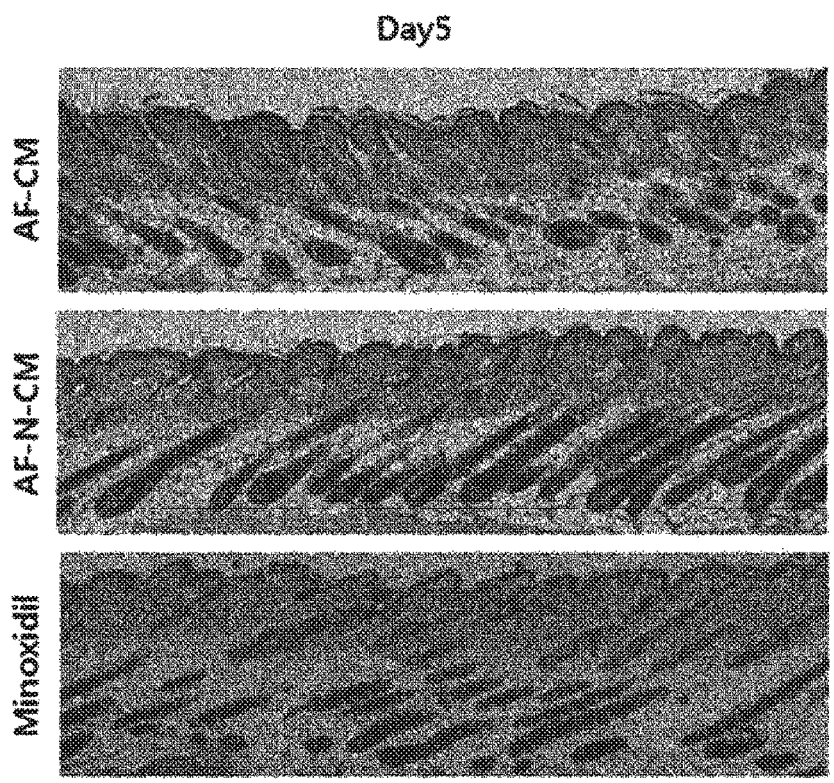
[Fig. 14]
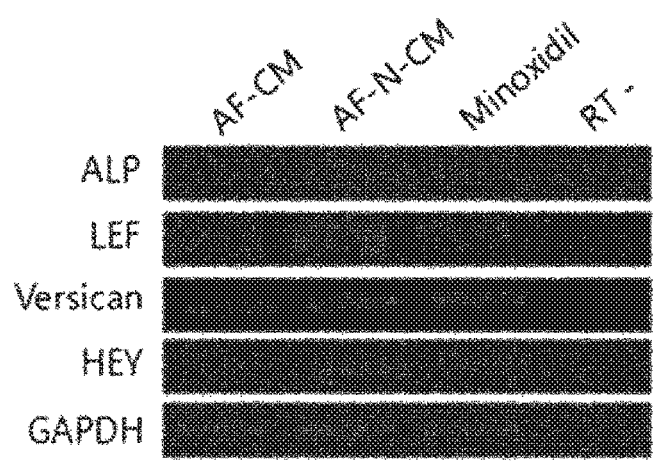

[Fig. 15]
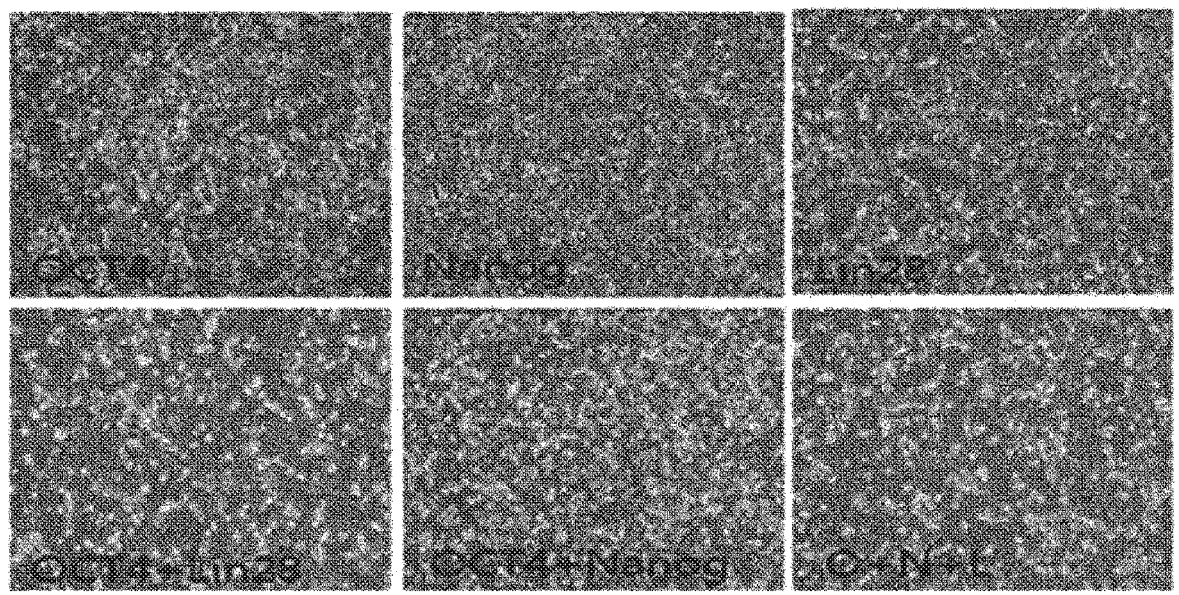

METHOD FOR PREPARING COMPOSITION FOR PROMOTING HAIR GROWTH USING NANOG-INTRODUCED MESENCHYMAL STEM CELLS DERIVED FROM FETUS IN AMNIOTIC FLUID

RELATED APPLICATIONS

This application is a National Phase of PCT Patent Application No. PCT/KR2016/010177 having International filing date of Sep. 9, 2016, which claims the benefit of priority of Korean Patent Application No. 10-2015-0130125, filed on Sep. 15, 2015. The contents of the above applications are all incorporated by reference as if fully set forth herein in their entirety.

SEQUENCE LISTING STATEMENT

The ASCII file, entitled 73379SequenceListing.txt, created on Mar. 15, 2018, comprising 8,924 bytes, submitted concurrently with the filing of this application is incorporated herein by reference. The sequence listing submitted herewith is identical to the sequence listing forming part of the international application.

FIELD AND BACKGROUND OF THE INVENTION

The present invention relates to a composition for promoting hair growth, which includes a culture solution of mesenchymal stem cells derived from a fetus in amniotic fluid in which a reverse-transcription factor, Nanog, is overexpressed as an active ingredient, and a method for preparing the same.

Stem cells are cells having an ability to differentiate into various types of cells constituting a body due to environments inside and outside the body and stimuli, and a self-replication ability, and there are three types of well-known stem cells, for example, embryonic stem cells (ES cells) isolated from early embryos, embryonic germ cells (EG cells) isolated from primordial germ cells in the embryonic phase, and multipotent adult progenitor cells (MAPC cells) isolated from adult bone marrow.

Bone marrow-derived mesenchymal stem cells, which are one type of adult stem cells, have been used for a long time, and their various effects have been proven. In addition, recently, it has been reported that cells isolated from adipose tissue or other types of tissue have similar characteristics to bone marrow-derived mesenchymal stem cells.

The inventors focused on amniotic fluid which is easily isolated from a pregnant woman or a fetus. They tested to obtain a variety of information about the health of the fetus from the amniotic fluid, and extracted the amniotic fluid without damaging the pregnant woman from the beginning of pregnancy up to immediately after the birth. The amniotic fluid cells used in the tests were disposed of after the test, and when a patient's consent was received, the cells could be used for study without disposal, and therefore, a large amount of the amniotic fluid cells can be easily acquired, compared to other adult stem cells that have been studied conventionally.

Meanwhile, since human hair has a unique growth cycle, that is, a hair cycle including: anagen phase→catagen phase→telogen phase→growth phase, a constant number of hairs is always maintained without molting. However, when baldness is progressing, a hair papilla present in a hair root becomes smaller, the thickness of hair is reduced, the hair cycle becomes shorter, and newly grown hair becomes thinner. Therefore, when baldness progresses, the hair turns into fluffy hair, has a shorter growth cycle, and then falls out after slightly growing. The major cause of baldness is heredity, and a male hormone, testosterone, is known to be involved in the expression of a baldness gene. Hair loss occurs in many cases because of aging, stress, etc., not because of genetically-occurring baldness. It has been known that aging-related hair loss is caused by poor blood circulation caused by pressed capillaries around pores, which is generated by a decrease in oxygen supply due to pore closure according to a decrease in scalp cells and an increase in accumulative amount of scalp fat. In addition, stress, an irregular lifestyle, and environmental pollution are also considered to cause baldness.

While the emotional pain felt by people with baldness or hair loss is very large, most hair restorers which have been developed and now commercially available have temporary or limited effects, and do not sufficiently satisfy users' needs. An applicable hair restorer, minoxidil, which has been proven to be effective to a certain extent due to vasodilation, and an oral hair restorer, Propecia, which contains finasteride as a main ingredient and exhibits its effect due to an inhibitory action on activation of a male hormone, have been widely used as agents having excellent effects in preventing hair loss. However, the above-mentioned hair restorers are effective in preventing hair loss to a certain extent, but exhibit insignificant effects on hair growth. That is, when the use of the hair restorers is stopped, hair loss reoccurs, and there are great concerns about side effects and increased costs due to long-term use. For this reason, most patients are giving up treatment.

Therefore, the inventors discovered reprogramming factors capable of extending the growth and lifespan of mesenchymal stem cells derived from a fetus in amniotic fluid and enhancing hair growth efficacy of a conditioned medium, and identified which components in the conditioned medium are effective for hair growth efficacy. In addition, the inventors confirmed effects of the conditioned medium on the promotion of the density of hair and hair growth through an in vivo experiment, and thus the present invention was completed.

SUMMARY OF THE INVENTION

The present invention is directed to providing a method for producing a human growth factor from Nanog-overexpressing mesenchymal stem cells derived from a fetus in amniotic fluid.

The present invention is directed to providing a method for preparing a composition for promoting hair growth, which includes a conditioned medium containing a human growth factor produced from Nanog-overexpressing mesenchymal stem cells derived from a fetus in amniotic fluid as an active ingredient.

The present invention is also directed to providing a composition for promoting hair growth, which includes a conditioned medium containing a human growth factor produced from Nanog-overexpressing mesenchymal stem cells derived from a fetus in amniotic fluid as an active ingredient, and a cosmetic or pharmaceutical composition thereof.

Hereinafter, the present invention will be described in detail.

The present invention provides a method for producing a human growth factor from Nanog-overexpressing mesenchymal stem cells derived from a fetus in amniotic fluid, and more particularly, to a method for producing any one or more human growth factors selected from the group consisting of a basic fibroblast growth factor (bFGF), an insulin-like growth factor (IGF), wingless-type MMTV integration site family member 7A (Wnt7a) and a platelet-derived growth factor (PDGF-AA) from Nanog-overexpressing mesenchymal stem cells derived from a fetus in amniotic fluid, and more specifically, a method for producing any one or more human growth factors selected from the group consisting of bFGF, IGF, Wnt7a and PDGF-AA from Nanog-overexpressing mesenchymal stem cells derived from a fetus in amniotic fluid, the method including:

(a) isolating fetal cells from the amniotic fluid obtained from a pregnant woman;

(b) obtaining mesenchymal stem cells derived from a fetus in amniotic fluid by subculturing the isolated fetal cells in a culture medium containing fetal bovine serum (FBS), bFGF, selenium and ascorbic acid;

(c) obtaining Nanog-overexpres sing mesenchymal stem cells derived from a fetus in amniotic fluid by introducing Nanog into the obtained mesenchymal stem cells derived from a fetus in amniotic fluid; and (d) preparing a conditioned medium containing any one or more human growth factors selected from the group consisting of bFGF, IGF, Wnt7a and PDGF-AA by culturing the obtained Nanog-overexpres sing mesenchymal stem cells derived from a fetus in amniotic fluid in a serum-free medium for 1 to 5 days.

In Step (a), the fetal cells may be included in the amniotic fluid obtained from a pregnant woman.

The term "mesenchymal stem cells (MSCs)" used herein refers to cells being the origin from which bone, cartilage, fat, the bone marrow stroma, muscle or nerve is generated, and cells that generally remain in the bone marrow in adults, but also present in cord blood, peripheral blood and other tissues, and obtained therefrom. Since amniotic fluid, which is obtained from a pregnant woman, contains various chemicals generated from a fetal body, most cells in a human body can be generated, and easily taken for sampling. In addition, it was confirmed that heterogenous cells are present in amniotic fluid, and among these cells, there are homogenous MSCs having the same shape as fibroblasts, which is a feature of the MSCs.

The term "culture medium" used herein refers to a medium that can sustain the growth and existence of fetal cells in amniotic fluid in vitro, and includes all media conventionally used in the art, which are suitable for culturing fetal cells in amniotic fluid. The culture medium and culture conditions may be selected according to the type of cells. The culture medium is preferably a cell culture minimum medium (CCMM), and generally includes a carbon source, a nitrogen source and trace elements. Such a CCMM includes Dulbecco's Modified Eagle's Medium (DMEM), Minimal Essential Medium (MEM), Basal Medium Eagle (BME), RPMI1640, F-10, F-12, α Minimal Essential Medium (αMEM), Glasgow's Minimal Essential Medium (GMEM) and Iscove's Modified Dulbecco's Medium (IMEM). In addition, the cell culture minimum medium (CCMM) may include an antibiotic such as penicillin, streptomycin or gentamicin.

In Step (b), the MSCs derived from a fetus in amniotic fluid may be obtained by culturing the cells isolated from the amniotic fluid in a basic medium containing FBS, bFGF, selenium and ascorbic acid, preferably, obtained by culturing the cells in FBS-containing low-glucose DMEM supplemented with bFGF, selenium and ascorbic acid, and more preferably, by culturing the cells in 10% FBS low-glucose DMEM supplemented with 4 ng/ml of bFGF, 5 ng/ml of selenium, 50 µg/ml of ascorbic acid, 1% L-glutamine and 1% penicillin-streptomycin, but the present invention is not limited thereto.

In Step (c), Nanog may be introduced using a retrovirus vector, and preferably, using a pMXs virus vector, but the present invention is not limited thereto.

In Step (c), Nanog may be a gene consisting of a base sequence represented by SEQ ID NO: 1, and preferably, a human (*Homo sapiens*)-derived Nanog gene, but the present invention is not limited thereto.

In an exemplary embodiment of the present invention, it was confirmed that the growth and proliferation of the MSCs are increased according to the step of introducing Nanog into the MSCs and culturing the cells.

The term "Nanog" used herein is a reprogramming factor, which originates from "reprogramming," which is a concept introduced by Prof. Yamanaka and his team in 2006. All adult tissues gradually become differentiated through a normal development process, and are changed to functionally-specified cells. Among these, cells of the fertilized egg are totipotent, and as being developed to become blastocysts, can be distinguished into inner cell mass cells and outer cells. The inner cell mass cells may generate embryonic somatic cells and germ cells, which is called pluripotency. The inner cell mass cells are also called embryonic stem cells, and express a pluripotency-specific gene (reprogramming factor). Specific examples of the genes are Oct4, Sox2, Nanog, and Lin28. Reprogramming is the technology of inducing the expression of such pluripotency-specific genes in somatic cells, and thus returning the cells to have similar properties to embryonic stem cells. According to such a background, the present invention independently used Nanog among various reprogramming factors. For this reason, 1) there is a concern about the change in cell characteristics when several foreign genes are introduced, 2) it is difficult to successfully construct cell lines when several factors are introduced using a virus, and 3) it is confirmed that, when Nanog is independently introduced, the cell lines can be continuously maintained (refer to FIG. 15).

In addition, the present invention provides a conditioned medium prepared by Step (d), more specifically, a conditioned medium prepared by culturing Nanog-overexpressing MSCs derived from a fetus in amniotic fluid, and further more specifically, a conditioned medium containing any one or more human growth factors selected from the group consisting of bFGF, IGF, Wnt7a and PDGF-AA to culture Nanog-overexpressing MSCs derived from a fetus in amniotic fluid.

The term "conditioned medium" used herein refers to a medium prepared by growing cells using liquid suspension culture, removing divided cells when the cells reach the exponential phase during cell division by centrifugation or filtration, thereby obtaining only a culture solution, and mixing the culture solution with a culture substrate. This medium uses an unknown growth factor extracted from dividing cells in the culture medium, and is widely used in low-density cell plating or protoplast culture.

The conditioned medium prepared in Step (d) is a medium prepared by removing the fetal MSCs from the culture medium in which the fetal MSCs are cultured, and abundantly containing materials like growth factors derived from the fetal MSCs.

In addition, the present invention provides a method for preparing a composition for promoting hair growth which includes a conditioned medium prepared by culturing Nanog-overexpressing MSCs derived from a fetus in amniotic fluid as an active ingredient, and more specifically, a method for preparing a composition for promoting hair growth which includes a conditioned medium containing any one or more human growth factors selected from the group consisting of bFGF, IGF, Wnt7a and PDGF-AA, produced from Nanog-overexpressing MSCs derived from a fetus in amniotic fluid, as an active ingredient, the method including:

(a) isolating fetal cells from the amniotic fluid obtained from a pregnant woman;

(b) obtaining MSCs derived from a fetus in amniotic fluid by subculturing the isolated fetal cells in a medium containing FBS, bFGF, selenium and ascorbic acid;

(c) obtaining Nanog-overexpressing MSCs derived from a fetus in amniotic fluid by introducing Nanog into the obtained MSCs derived from a fetus in amniotic fluid;

(d) preparing a conditioned medium containing any one or more human growth factors selected from the group consisting of bFGF, IGF, Wnt7a and PDGF-AA by culturing the obtained Nanog-overexpressing MSCs derived from a fetus in amniotic fluid in a serum-free medium for 1 to 5 days; and (e) preparing a composition including the prepared conditioned medium as an active ingredient.

The term "promotion of hair growth" used herein refers to promotion of hair growth according to a hair growth effect and the promotion of a hair growth phase.

The conditioned medium prepared in Step (d) may contain a human growth factor such as bFGF, IGF, PDGF-AA, Wnt7a, or a combination of two or more thereof, but the present invention is not limited thereto. The bFGF (Du Cros et al. Fibroblast growth factor and epidermal growth factor in hair development. J Invest Dermalto. 101:106S-113S, 1993), IGF (Nicole et al. IGF-I signaling controls the hair growth cycle and the differentiation of hair shafts. J Invest Dermalto 125:873-882, 2005), PDGF-AA (Tomita et al. PDGF isoforms induce and maintain anagen phase of murine hair follicles. Journal of dermatological science 43(2):105-15, 2006) or Wnt7a (Kishimoto et al. Wnt signaling maintains the hair-inducing activity of the dermal papilla. Genes & Development 14:1191-1185, 2000) has been known as a growth factor that stimulates hair growth.

In addition, the conditioned medium prepared in Step (d) may further include a growth factor such as apoptosis antigen 1 (Apo-1)/Fas, epidermal growth factor (EGF), interferon-γ inducible protein-10 (IP-10), leptin, macrophage inflammatory protein 4 (MIP4), matrix metalloproteinase 3 (MMP3), Rantes, interferon γ (IFNγ), transforming growth factor β (TGFβ), tumor necrosis factor α (TNFα), tumor necrosis factor receptor □ (TNFR □), tumor necrosis factor receptor □ (TNFR □), intercellular Adhesion Molecule 1 (ICAM1), vascular cell adhesion molecule 1 (VCAM1), a vascular endothelial growth factor, interleukin-1β (IL-1β), interleukin-1 receptor α (IL-1Rα), IL-2, IL-3, IL-4, IL-5, IL-6, IL-6R, IL-7, IL-8, IL-12, or IL-15, but it has been known that the hair growth promoting effect of such a growth factor has not been proven.

Therefore, using a method for preparing a composition for promoting hair growth including the conditioned medium as an active ingredient, the expression level of a growth factor such as bFGF, IGF, Wnt7a, PDFG-AA, or a combination of two or more thereof, which has been known to have a hair growth effect, is considerably increased, and therefore an effect of enhancing hair growth may be further increased.

In an exemplary embodiment of the present invention, it was confirmed that a large amount of hair follicle tissue is generated in a conditioned medium-treated group obtained from Nanog-introduced amniotic fluid-derived MSCs, shows the shape formed in a later step of growth phase when steps of the growth phase are distinguished in histological analysis, and also confirmed that mRNAs of amplified length polymorphism (ALP), LEF, Versican and Hey which are highly expressed in the hair growth phase.

In addition, the present invention provides a composition for promoting hair growth including a conditioned medium prepared by culturing Nanog-overexpres sing MSCs derived from a fetus in amniotic fluid as an active ingredient, specifically, a composition for promoting hair growth, which includes a conditioned medium containing any one or more human growth factors selected from the group consisting of bFGF, IGF, Wnt7a and PDFG-AA produced from Nanog-overexpressing MSCs derived from a fetus in amniotic fluid as an active ingredient, and more specifically, a composition for promoting hair growth prepared by the method for preparing a composition for promoting hair growth.

In an exemplary embodiment of the present invention, it was confirmed that a conditioned medium prepared by culturing Nanog-overexpressing amniotic fluid-derived MSCs shows considerably increased expression levels of hair growth promoters in the medium, and rapid hair growth when mice are treated with the medium, resulting in promotion of hair growth, regeneration of hair and prevention of hair loss.

In addition, the present invention provides a cosmetic composition for promoting hair growth, which includes the composition for promoting hair growth.

The cosmetic composition may be variously used in hair cosmetic products that are effective in promotion of hair growth, hair regeneration and prevention of hair loss.

The cosmetic composition may be included at 0.001 to 10 parts by weight with respect to 100 parts by weight of the total cosmetic composition.

The cosmetic composition may contain a lipid material, an organic solvent, a solubilizer, a thickener, a gelating agent, a softener, an antioxidant, a suspending agent, a stabilizer, a foaming agent, a fragrance, a surfactant, water, an ionic or non-ionic emulsifier, a filler, a metal ion sequestering agent, a chelating agent, a preservative, a vitamin, a blocking agent, a wetting agent, an essential oil, a dye, a pigment, a hydrophilic or lyophilic activating agent, or an additive conventionally used in a cosmetological or dermatological field such as any other components conventionally used in lipid vesicles or cosmetic products. The additive is introduced at an amount that is generally used in a cosmetological or dermatological field.

A product of the cosmetic composition contains a cosmetological or dermatologically-acceptable medium or substrate. It may be prepared in all formulations suitable for local application, for example, a solution, a gel, a solid, an anhydrous paste product, an emulsion obtained by dispersing an oil phase in an aqueous phase, a suspension, a microemulsion, a microcapsule, a micro granulocyte or an ionic (liposome) and non-ionic vesicular dispersing agent, a cream, a skin softener, a lotion, a powder, a salve, a spray or a concealer stick. The composition may be prepared by a method conventionally used in the art. The composition according to the present invention may also be used in the form of a foam or an aerosol composition further containing a compressed propellant.

The cosmetic composition of the present invention is not particularly limited in its formulation, and may be formulated as a cosmetic product, for example, a moisturizing lotion, an astringent, a nourishing lotion, a nourishing cream, a massage cream, an essence, an eye cream, an eye essence, a cleansing cream, a cleansing foam, a cleansing water, a pack, a powder, a body lotion, a body cream, a body oil, a body essence, a hair tonic, a hair conditioner, a hair essence, a hair lotion, a hair nourishing lotion, a hair shampoo, a hair rinse, a hair treatment, a hair cream, a hair nourishing cream, a hair moisturizing cream, a hair massage cream, a hair wax, a hair aerosol, a hair pack, a hair nourishing pack, a hair soap, a hair cleansing foam, a hair oil, a hair drying preparation, a hair preservation treatment, a hair colorant, a hair waving preparation, a hair decolorant, a hair gel, a hair glaze, a hair dressing, a hair lacquer, a hair moisturizer, a hair mousse or a hair spray.

The cosmetic composition as described above may be applied onto skin, or applied to be absorbed into skin using microneedles.

In addition, the present invention provides a pharmaceutical composition for promoting hair growth, which includes the composition for promoting hair growth.

The pharmaceutical composition may be variously used in hair cosmetic products which are effective in promoting hair growth, hair regeneration and preventing hair loss.

The pharmaceutical composition may be included at 0.001 to 10 parts by weight with respect to 100 parts by weight of the total pharmaceutical composition.

The pharmaceutical composition may be prepared as tablets, capsules, powder, granules, injections, gels, emulsions, syrups, aerosols, patches, sprays, creams, ointments, plasters, lotions, liniments, pastes or cataplasmas for promoting hair growth, but the present invention is not limited thereto.

When the pharmaceutical composition is prepared, a filler, a thickener, a binder, a wetting agent, a disintegrating agent, a diluent such as a surfactant or an excipient, is ordinarily used. Solid preparations for oral administration include tablets, pills, powders, granules, capsules, and are prepared by mixing one or more compounds with at least one or more excipients, for example, starch, calcium carbonate, sucrose, lactose, or gelatin. In addition, other than simple excipients, lubricants such as magnesium stearate, talc, etc. are also used. Liquid preparations for oral administration may include suspending agents, liquids for internal use, emulsions, syrups, etc., and other than frequently used simple diluents such as water or liquid paraffin, various excipients, e.g., wetting agents, sweetening agents, fragrances, preservatives, etc. Preparations for parenteral administration include sterilized aqueous solutions, non-aqueous solvents, suspending agents, emulsions, lyophilizing agents, and suppositories. As a non-aqueous solvent or a suspending solvent, propylene glycol, polyethylene glycol, a vegetable oil such as olive oil, or an injectable ester such as ethyl oleate may be used. As the base of a suppository, Witepsol, Microgol, Tween 61, Cacao butter, laurinum, or glycerogelatin may be used.

The pharmaceutical composition may be administered as a pharmaceutically acceptable salt thereof, alone or in combination with a different pharmaceutically active compound, or a suitable set thereof. The salt is not limited to a specific type, and may be any pharmaceutically acceptable salt, for example, hydrochloric acid, sulfuric acid, nitric acid, phosphoric acid, hydrofluoric acid, hydrobromic acid, formic acid, acetic acid, tartaric acid, lactic acid, citric acid, fumaric acid, maleic acid, succinic acid, methanesulfonic acid, benzenesulfonic acid, toluenesulfonic acid, or naphthalene sulfonic acid.

The pharmaceutical composition may be administered parenterally or orally according to a purpose and administered once or several times at a daily dose of 0.1 to 500 mg, and preferably 1 to 100 mg per kg of a body weight. A dosage for a specific patient may vary according to a patient's body weight, age, sex, health condition, diet, administration time, administration method, administration route, excretion rate, and severity of a disease.

The pharmaceutical composition may be administered via various routes, for example, parenterally or orally, to mammals such as rats, mice, livestock and humans. All administration routes can be expected, and administration may be carried out orally, or by rectal, intravenous, intramuscular, subcutaneous, intrauterine, epidural or intracerebroventricular injection.

The major limitation in production of a conditioned medium of MSCs is highly associated with aging of the stem cells. The cell aging induces low cell growth, reduces amounts of a growth factor and cytokine, and causes cell death. In addition, the cell aging also induces quantitative and qualitative losses of a cell-derived conditioned medium, and makes it difficult to maintain a uniform composition, resulting in difficulties in mass-production and industrialization of a conditioned medium and a composition including the same as an active ingredient. Therefore, the inventors introduced reprogramming technology to culture MSCs. According to previous research, it has been known that a change in the aspect of stemness according to the expression of pluripotent factors in MSCs occurs. In this regard, various pluripotent factors, Oct4, Nanog and Lin28, were introduced to amniotic fluid-derived MSCs, and among these, it was seen that the Nanog-introduced amniotic fluid-derived MSCs can be established as a cell line and continuously cultured, but the introduction of other genes induced cell death and it was difficult to continuously culture cells (refer to FIG. 15). Moreover, it was confirmed that the Nanog-introduced amniotic fluid stem cells were further improved in effects of enhancing cell growth and conserving stemness than conventional amniotic fluid stem cells.

In an exemplary embodiment of the present invention, it was confirmed that, since the number of Nanog-introduced amniotic fluid-derived MSCs is considerably higher than the amniotic fluid-derived stem cells (FIG. 4), Nanog has a positive effect on the improvement in growth of the amniotic fluid-derived MSCs. The Nanog-introduced amniotic fluid-derived MSCs less expressed β-galactosidase (left of FIG. 5), and exhibited lower expression levels of p53 and p21 (right of FIG. 5) than the amniotic fluid-derived MSCs. Therefore, it was confirmed that, due to the introduction of Nanog, there is an effect of extending the lifespan of the amniotic fluid-derived MSCs. In addition, the expression of pluripotency-specific markers, Oct4 and Sox2, was enhanced in the Nanog-introduced amniotic fluid-derived MSCs (FIG. 7), and thus, even by the introduction of Nanog, stemness of the amniotic fluid-derived MSCs is conserved.

In an exemplary embodiment of the present invention, it was confirmed that, in the Nanog-introduced amniotic fluid-derived MSCs, the expression of growth factors promoting hair growth, bFGF, IGF, Wnt7a and PDGF-AA was increased, compared to the amniotic fluid-derived MSCs (FIGS. 8 and 9), and due to the introduction of Nanog, the secretion of the hair growth factors was promoted in the amniotic fluid-derived MSCs.

In an exemplary embodiment of the present invention, it was observed that more hair follicle tissue is produced in a conditioned medium-treated group, which is obtained from the Nanog-introduced amniotic fluid-derived MSCs (FIG. 12). In addition, when steps of a growth phase were distinguished in histological analysis, it was confirmed that a group treated with a conditioned medium of Nanog-introduced amniotic fluid-derived MSCs shows a shape in the later step of the growth phase (FIG. 13), and mRNAs of amplified length polymorphism (ALP), LEF, Versican and Hey, which are highly expressed in the hair growth step, are much highly expressed in the group treated with the conditioned medium of Nanog-introduced amniotic fluid-derived MSCs (FIG. 14). Therefore, it was confirmed that, when the conditioned medium of the Nanog-introduced amniotic fluid-derived MSCs was applied, hair growth promoting effects were exhibited in vitro and in vivo.

In the present invention, as a reprogramming factor Nanog is introduced and overexpressed in MSCs derived from a fetus in amniotic fluid, the growth, stemness and lifespan of the MSCs are improved, and the expression of a growth factor, which is secreted from the cells, is increased. In addition, since a conditioned medium prepared by culturing Nanog-introduced MSCs derived from a fetus in amniotic fluid exhibits a hair growth promoting effect, the cells can be used as cosmetic and pharmaceutical compositions for promoting hair growth.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a graph showing that growth of amniotic fluid-derived MSCs is improved when amniotic fluid-derived cells are cultured with low glucose DMEM, 10% FBS, bFGF, selenium and ascorbic acid; b: bFGF-containing medium, by: bFGF and ascorbic acid-containing medium, bs: bFGF and selenium-containing medium, bvs: bFGF, ascorbic acid and selenium-containing medium;

FIG. 2 is a set of images showing shapes of conventional amniotic fluid-derived MSCs and Nanog-introduced amniotic fluid-derived MSCs; normal AF: amniotic fluid-derived MSCs, AF-Nanog: Nanog-introduced amniotic fluid-derived MSCs;

FIG. 3 is a set of images showing the results of RT-PCR (left) and immunofluorescence staining (right) to confirm Nanog overexpression in Nanog-introduced amniotic fluid-derived MSCs; left: AFSC: amniotic fluid-derived MSCs, AF-N #1, #2, #3: Nanog-introduced amniotic fluid-derived MSCs, right: AFSC: amniotic fluid-derived MSCs, AF-Nanog: Nanog-introduced amniotic fluid-derived MSCs;

FIG. 4 is a graph of growth curves of amniotic fluid-derived MSCs and Nanog-introduced amniotic fluid-derived mesenchymal stem cell lines (#1, #2, #3); normal AF: amniotic fluid-derived MSCs, AF-N #1, #2, #3: Nanog-introduced amniotic fluid-derived MSCs;

FIG. 5 is a set of images showing the results of β-galactosidase staining (left) and p53 and p21 mRNA expression levels (right) of Nanog-introduced amniotic fluid-derived MSCs (after 35 subcultures); left: AF-N #1, #2, #3: Nanog-introduced amniotic fluid-derived MSCs, normal AF: amniotic fluid-derived MSCs, right: AF: amniotic fluid-derived MSCs, AF-N: Nanog-introduced amniotic fluid-derived MSCs, RT(−): negative control capable of detecting dimer formation between primers;

FIG. 6 is an image showing the expression of mesenchymal stem cell-specific markers (Fibronectin, MMP1, Snail, Slug), obtained by RT-PCR, to prove that the characteristics of Nanog-introduced amniotic fluid-derived MSCs are not changed; AF-normal: amniotic fluid-derived MSCs, AF-N: Nanog-introduced amniotic fluid-derived MSCs;

FIG. 7 is a set of graphs showing expression levels of pluripotent genes Oct4 and Sox2 in Nanog-introduced amniotic fluid-derived MSCs; AF: amniotic fluid-derived MSCs, AF-N: Nanog-introduced amniotic fluid-derived MSCs;

FIG. 8 is a set of graphs showing expression levels of growth factors bFGF, IGF, Wnt7a and PDGF-AA in Nanog-introduced amniotic fluid-derived MSCs; AF: amniotic fluid-derived MSCs, AF-N: Nanog-introduced amniotic fluid-derived MSCs;

FIG. 9 is an image of the result of western blotting (top) showing expression levels of growth factors bFGF, IGF, Wnt7a and PDGF-AA in Nanog-introduced amniotic fluid-derived MSCs, and a set of graphs showing the results of ELISA (bottom) showing expression levels of bFGF and PDGF in a conditioned medium prepared by culturing Nanog-introduced amniotic fluid-derived MSCs; AF: amniotic fluid-derived MSCs, AF-N: Nanog-introduced amniotic fluid-derived MSCs, AF CM: conditioned medium prepared by culturing Nanog-introduced amniotic fluid-derived MSCs, AF-N CM: conditioned medium prepared by culturing Nanog-introduced amniotic fluid-derived MSCs;

FIG. 10 is a graph showing cell growth rates after hair follicle cells are treated with conditioned media in which amniotic fluid-derived MSCs and Nanog-introduced amniotic fluid-derived MSCs are cultured, respectively; AF CM: conditioned medium prepared by culturing amniotic fluid-derived MSCs, AF-N CM: conditioned medium prepared by culturing Nanog-introduced amniotic fluid-derived MSCs, Minox (minoxidil): positive control;

FIG. 11 is a set of images showing degrees of hair growth after conditioned media in which amniotic fluid-derived MSCs and Nanog-introduced amniotic fluid-derived MSCs are cultured, respectively, are applied to the back of shaved mice; AF-CM: conditioned medium prepared by culturing amniotic fluid-derived MSCs, AF-N-CM: conditioned medium prepared by Nanog-introduced amniotic fluid-derived MSCs, Minox (minoxidil): positive control;

FIG. 12 is a set of images showing the results of H&E staining (top) and numbers of hair follicles (bottom) for hair follicle tissue of mice treated with conditioned media in which amniotic fluid-derived MSCs and Nanog-introduced amniotic fluid-derived MSCs are cultured, respectively; AF-CM: conditioned medium prepared by culturing amniotic fluid-derived MSCs, AF-N-CM: conditioned medium prepared by culturing Nanog-introduced amniotic fluid-derived MSCs;

FIG. 13 is a set of images showing the results of H&E staining for murine dermal tissue treated with conditioned media in which amniotic fluid-derived MSCs and Nanog-introduced amniotic fluid-derived MSC are cultured, respectively; AF-CM: conditioned medium prepared by culturing amniotic fluid-derived MSCs, AF-N-CM: conditioned medium prepared by culturing Nanog-introduced amniotic fluid-derived MSCs, Minoxidil: positive control;

FIG. 14 is an image showing mRNA expression levels of hair formation-specific markers ALP, LEF, Versican and Hey in murine dermal tissue treated with conditioned media in which amniotic fluid-derived MSCs and Nanog-introduced amniotic fluid-derived MSC are cultured, respectively; AF-CM: conditioned medium prepared by culturing amniotic fluid-derived MSCs, AF-N-CM: conditioned medium prepared by culturing Nanog-introduced amniotic fluid-derived MSCs, Minoxidil: positive control, Reverse transcription (RT): negative control capable of detecting dimer formation between primers; and FIG. 15 is a set of images taken by a microscope (Olympus DP70) with magnification of 40×, showing the result of an experiment to confirm whether continuous culture is possible after several pluripotent genes are introduced into amniotic fluid-derived MSCs; Oct4: introduction of Oct4 only, Nanog: introduction of Nanog only, Lin28: introduction of Lin28 only, Oct4+Lin28: introduction of Oct4 and Lin28, Oct4+Nanog: introduction of Oct4 and Nanog, O+N+L: introduction of Oct4, Nanog and Lin28.

DESCRIPTION OF SPECIFIC EMBODIMENTS OF THE INVENTION

Hereinafter, the present invention will be described in detail with reference to examples to help in understanding of the present invention. However, the following examples are merely provided to illustrate the present invention, and the scope of the present invention is not limited thereto. The examples of the present invention are provided to more fully describe the present invention to those of ordinary skill in the art.

Example 1

Isolation and Culturing of Amniotic Fluid-Derived MSCs

MSCs derived from a fetus in amniotic fluid were obtained by subculturing fetal cells isolated from the amniotic fluid obtained from a pregnant woman in low-glucose Dulbecco's Modified Eagle's Medium (DMEM) containing 10% FBS, 1% penicillin/streptomycin, 1% L-glutamine, 4 ng/ml of bFGF, 5 ng/ml of selenium and 50 µg/ml of ascorbic acid. Such a condition for the medium exhibited a further improved effect of growing amniotic fluid-derived MSCs than bFGF-treated, bFGF and selenium-treated, bFGF and ascorbic acid-treated conditions (FIG. 1).

The effect of growing the amniotic fluid-derived MSCs was evaluated by examining a growth rate after the cells were cultured for 2 to 4 days, and quantification was performed by crystal violet staining. Samples of the same number of cells were prepared, and then 10% formalin fixation was performed at intervals of two days or four days, and then the crystal violet staining was performed on the cells for 20 minutes. The cells were destained with 10% acetic acid, and quantitative analysis was carried out by measuring the absorbance of acetic acid at 595 nm using an Ultrospec 2100pro spectrophotometer.

The obtained MSCs derived from a fetus in amniotic fluid were cultured in DMEM under the same conditions as described above.

Example 2

Preparation of Nanog-Introduced Amniotic Fluid-Derived MSCs

Nanog-introduced amniotic fluid-derived mesenchymal stem cell lines (#1, #2, #3) were prepared by introducing a Nanog gene into the amniotic fluid-derived MSCs obtained in Example 1 using a retroviral vector system to induce Nanog overexpression (FIG. 2).

Specifically, a Nanog gene (NCBI GenBank Accession number NM_024865.3; SEQ ID NO: 1) was isolated from a pBS-Nanog vector (Yamanaka lab's plasmid stock # A4, Japan) with a restriction enzyme. The isolated Nanog gene was ligated into a pMXs vector (Cell Biolabs, Japan) using a T4 ligase, thereby manufacturing pMXs-Nanog. The pMXs-Nanog vector was transfected into 293GPG cells using a transfection reagent for 6 hours. For 72 hours, viruses having Nanog gene were produced, and a supernatant was isolated, centrifuged at 2000 rpm for 10 minutes and filtered using a 0.45-µm filter. The viruses were introduced to the amniotic fluid-derived MSCs grown to 80% confluence for 6 hours, resulting in infection into the cells.

When the prepared Nanog-introduced amniotic fluid-derived MSCs were cultured in the medium of Example 1, the cells were continuously and normally grown.

Example 3

Assay for Confirming Nanog Expression of Nanog-Introduced Amniotic Fluid-Derived MSCs To confirm whether Nanog overexpression in the Nanog-introduced amniotic fluid-derived MSC lines (#1, #2, #3) prepared in Example 2 properly occurred, reverse transcription polymerase chain reaction (RT-PCR) and immunofluorescence staining were performed on Nanog mRNA.

To perform RT-PCR, the Nanog-introduced amniotic fluid-derived MSCs were treated with a TRIzol reagent (Invitrogen, USA) to isolate total RNA according to the manufacturer's protocol. 500 µg of the isolated total RNA was reverse-transcripted to cRNA using a cDNA preparation mix (Bioneer). Test tubes were maintained at 45□ for 60 minutes, maintained at 95□ for 5 minutes, and then stored at −20□ for use afterward. cDNA was amplified using a Taq polymerase (Promega) and primers (Exo-Nanog forward: 5'-GCTTGGATACACGCCGC-3' (SEQ ID NO: 2); and Exo-Nanog reverse: 5'-GATTGTTCCAGGATTGGGTG-3' (SEQ ID NO: 3)) specific for Nanog mRNA. RT-PCR was repeatedly performed at 35 cycles at 94□ for 20 seconds, 60□ for 30 seconds, and 72□ for 2 minutes, and further performed at 72□ for 10 minutes for final synthesis. A PCR product was analyzed by electrophoresis in 1% agarose gel.

For immunofluorescence staining, the Nanog-introduced amniotic fluid-derived MSCs were washed with PBS, fixed with 4% paraformaldehyde for 1 hour, and washed with 0.5% Triton-100-added phosphate-buffered saline (PBS) (0.5% PBST) three times for 5 minutes each. The cells were blocked with 3% FBS-containing PBST for 1 hour, and treated with an antibody (AF276, R&D), which detects a Nanog receptor, at a ratio of 1:50 for 1 hour. Afterward, the cells were washed with 0.5% PBST three times for 5 minutes each, and then a fluorescence-tagged secondary antibody (Alexa Fluor 488 goat anti-human IgG, # A11013, Invitrogen, USA), following being diluted at a ratio of 1:200 was treated for 1 hour. After being treated with a 4',6-diamidino-2-phenylindole (DAPI) solution at 1:1000 for 5 minutes for nuclear staining, the cells were washed with PBST three times in the same manner as described above. Afterward, the sample was visualized using a fluorescence microscope (Olympus DP70).

As a result, compared to the amniotic fluid-derived MSCs, the Nanog-introduced amniotic fluid-derived MSCs showed a considerably increased expression level of an exogenous Nanog gene at an mRNA level and Nanog expression level at a protein level, confirming the overexpression of the Nanog gene (FIG. 3).

Example 4

Test for Confirming Effect of Improving Cell Growth of Nanog-Introduced Amniotic Fluid-Derived MSCs Growth rates of the Nanog-introduced amniotic fluid-derived mesenchymal stem cell lines (#1, #2, #3) prepared in Example 2 and the amniotic fluid-derived stem cells continuously cultured in the medium of Example 1 without Nanog introduction were compared and analyzed.

The stem cells were subcultured 13 times using the medium of Example 1, and a cell count of each cell line was measured using a Counting chamber (MARIENFELD, Germany) at intervals of three days, followed by comparison.

As a result, it was confirmed that the cell count of the Nanog-introduced amniotic fluid-derived MSCs was considerably higher than the amniotic fluid-derived stem cells (FIG. 4). This result showed that Nanog has a positive effect on the improvement in cell growth of the amniotic fluid-derived MSCs.

Example 5

Test for Confirming Effect of Extending Lifespan of Nanog-Introduced Amniotic Fluid-Derived MSCs To test the lifespan of the Nanog-introduced amniotic fluid-derived MSCs, a degree of cell death caused by continuous subculture was analyzed by β-galactosidase staining and mRNA expression levels of cell death-related proteins p53 and p21.

For β-galactosidase staining, the Nanog-introduced amniotic fluid-derived MSCs subcultured 35 times in the medium of Example 1 were seeded in a 6-well plate at a density of $5 \times 10^4$ cells/well, attached overnight, washed with PBS, and then fixed. A pH 6.0 X-gal chromogenic substrate was cultured overnight at 37□ according to the protocol of a β-galactosidase staining kit (Cell Signaling Technology, Beverly, Mass.), and then a color change was observed using a microscope (Olympus DP70) with a magnification of 100×.

To measure the mRNA expression levels of the cell death-related proteins p53 and p21, total RNA was extracted from the Nanog-introduced amniotic fluid-derived MSCs subcultured 35 times by the same method as described in Example 3, and from the total RNA, cDNA was amplified. cDNA was amplified with a Taq polymerase (Promega) and primers specific to mRNAs of p53, p21 and glyceraldehyde-3-phosphate dehydrogenase (GAPDH). The p53-specific primers were a p53 forward primer: 5'-CCTCACCATCAT-CACACTGG-3' (SEQ ID NO: 4) and a p53 reverse primer: 5'-TTATGGCGGGAGGTAGACTG-3' (SEQ ID NO: 5), the p21-specific primers were a p21 forward primer: 5'-GGAAGACCATGTGGACCTGT-3' (SEQ ID NO: 6) and a p21 reverse primer: 5'-AGGCAGAAGATGTAGAGCGG-3' (SEQ ID NO: 7), and the GAPDH-specific primers were a GAPDH forward primer: 5'-GTGGTCTCCTCTGACT-TCAACA-3' (SEQ ID NO: 8) and a GAPDG reverse primer: 5'-CTCTTCCTCTTGTGCTCTTGCT-3' (SEQ ID NO: 9). A PCR product was analyzed by electrophoresis in 1% agarose gel, and a relative mRNA expression level was quantified using Quantity One software based on GAPDH mRNA.

As a result, it was confirmed that the β-galactosidase was less expressed (left of FIG. 5), and p53 and p21 expression levels were decreased (right of FIG. 5) in the amniotic fluid-derived MSCs continuously subcultured in the medium of Example 1 after Nanog introduction than in the amniotic fluid-derived MSCs continuously subcultured in the same medium as Example 1 without Nanog introduction. Therefore, it was confirmed that the Nanog introduction leads to an effect of extending the lifespan of the amniotic fluid-derived MSCs.

Example 6

Confirmation of Change in Unique Characteristics of Nanog-Introduced Amniotic Fluid-Derived MSCs To confirm whether the expression of an expression marker specific for stem cells was changed due to the Nanog introduction, fibronectin, MMP1, Snail and Slug expression patterns were determined by RT-PCR.

For RT-PCR, RNA extraction and PCR were carried out by the same method as described in Example 3, and primers used herein are as follows. Fibronectin-specific primers were an Fibronectin forward primer: 5'-GACGACTC-CCTTTTCTCCTCTT-3' (SEQ ID NO: 10) and an Fibronectin reverse primer: 5'-TGAGTTCTGTGCTGCTACCTTC-3' (SEQ ID NO: 11), MMP1-specific primers were an MMP1 forward primer: 5'-TTGAGAAAGCCTTCCAACTCTG-3' (SEQ ID NO: 12) and an MMP1 reverse primer: 5'-CCG-CAACACGATGTAAGTTGTA-3' (SEQ ID NO: 13), Snail-specific primers were a Snail forward primer: 5'-CTCCT-TCGTCCTTCTCCTCTACTT-3' (SEQ ID NO: 14) and a Snail reverse primer: 5'-TCTTGACATCT-GAGTGGGTCTG-3' (SEQ ID NO: 15), and Slug-specific primers were a Slug forward primer: 5'-GACCCTGGTT-GCTTCAAGGACA-3' (SEQ ID NO: 16) and a Slug reverse primer: 5'-TTGTCATTTGGCTTCGGAGTGA-3' (SEQ ID NO: 17).

According to the result of RT-PCR, it was confirmed that there was no difference in expression of the MSC-specific marker between the Nanog-introduced amniotic fluid-derived MSCs and the amniotic fluid-derived MSCs (FIG. 6). Therefore, the Nanog introduction did not have much of an effect on the unique characteristics of the amniotic fluid-derived MSCs.

Example 7

Test for Confirming Expression of Pluripotent Gene in Nanog-Introduced Amniotic Fluid-Derived MSCs Multipotent stem cells have been known to express small amounts of pluripotency-specific markers Oct4 and Sox2 (Riekstina et al. Embryonic stem cell marker expression pattern in human MSCs derived from bone marrow, adipose tissue, heart and dermis. Stem cell rep 5(4):378-386. (2009)). To confirm whether a pluripotent gene is expressed in stem cells due to the Nanog introduction, mRNA expression levels of the Nanog-introduced amniotic fluid-derived MSCs Oct4 and Sox2 prepared in Example 2 were analyzed by quantitative reverse transcription polymerase chain reaction (qRT-PCR).

The qRT-PCR was carried out in the same manner as the RNA prep in RT-PCR described above, thereby obtaining RNA, and manufacturing cDNA. The cDNA prepared thereby was subjected to qRT-PCR using a CFX-96 PCR system, and amplified using primers specific to mRNAs of Oct4 and Sox2. Oct4-specific primers were an Oct4 forward primer: 5'-GACAGGGGGAGGGGAGGAGCTAGG-3' (SEQ ID NO: 18) and an Oct4 reverse primer: 5'-CTTC-CCTCCAACCAGTTGCCCCAAAC-3' (SEQ ID NO: 19), and Sox2-specific primers were a Sox2 forward primer: 5'-ACCAATCCCATCCACACTCACGCA-3' (SEQ ID NO: 20) and a Sox2 reverse primer: 5'-GCAAACTTCCTG-CAAAGCTCCTACCG-3' (SEQ ID NO: 21). A relative quantity of target mRNA was analyzed by comparative threshold (CT) cycling (Johnson M R., et al., Anal Biochem 2000; 278: 175-184).

As a result, it was confirmed that the expression of pluripotency-specific markers Oct4 and Sox2 was further enhanced in the Nanog-introduced amniotic fluid-derived MSCs (FIG. 7). Therefore, the expression of a pluripotency-specific gene in the amniotic fluid-derived MSCs was increased due to the Nanog introduction.

Example 8

Test for Confirming Expression of Hair Growth Factor in Amniotic Fluid-Derived MSCs Due to Nanog Overexpression To confirm the expression of a hair growth factor in the Nanog-introduced amniotic fluid-derived MSCs, mRNA expression levels and protein expression levels of the hair-related growth factors such as bFGF, IGF, Wnt7a and PDGF-AA were analyzed by qRT-PCR and western blotting.

The qRT-PCR was performed by the same method as described in Example 7, and cDNA was amplified using primers specific to mRNAs of bFGF, IGF, Wnt7a and PDGF-AA. The bFGF-specific primers were a bFGF forward primer: 5'-CAGATTAGCGGACGCGGTGC-3' (SEQ ID NO: 22) and a bFGF reverse primer: 5'-TCACGGATGGGTGTCTCCGC-3' (SEQ ID NO: 23), the IGF-specific primers were an IGF forward primer: 5'-CCATGTCCTCCTCGCATCTCTTCT-3' (SEQ ID NO: 24) and an IGF reverse primer: 5'-CCATACCCTGTGGGCTTGTTGAA-3' (SEQ ID NO: 25), the Wnt7a-specific primers were a Wnt7a forward primer: 5'-TCTTTCTCAGCCTGGGCATGGT-3' (SEQ ID NO: 26) and a Wnt7a reverse primer: 5'-TCCTATGACGATGATGGCGTCG-3' (SEQ ID NO: 27), and PDFG-AA-specific primers were a PDGF-AA forward primer: 5'-CTGCCCATTCGGAGGAAGAGAA-3' (SEQ ID NO: 28) and a PDGF-AA reverse primer: 5'-TGGCACTTGACACTGCTCGTGTT-3' (SEQ ID NO: 29). A relative quantity of target mRNA was analyzed by a CT method.

To perform western blotting on bFGF, IGF, Wnt7a and PDGF-AA, the Nanog-introduced amniotic fluid-derived MSCs were obtained after being cultured in 10% FBS-containing DMEM to be grown until 100% confluence and disrupted, and then 30 µg of a supernatant containing a protein was developed by sodium dodecyl sulfate-polyacrylamide gel electrophoresis (SDS-PAGE) to isolate the protein. The protein was transferred to a nitrocellulose membrane, and blocked with 4% skim milk. Afterward, the membrane was treated with primary antibodies such as an anti-bFGF antibody (Santa Cruz Biotechnology, USA), an anti-IGF antibody (Santa Cruz Biotechnology, USA), an anti-Wnt7a antibody (Santa Cruz Biotechnology, USA) and an anti-PDGF-AA antibody (Millipore, Germany), cultured overnight at 4□, and washed with TBST (0.1% Tween 20-added Tris-buffered saline (TBS)). The membrane was treated with a mouse and goat-derived anti-murine IgG antibody (goat anti-mouse IgG; Santa Cruz Biotechnology, USA) as a secondary antibody and 1% bovine serum albumin (BSA)-containing TBST, cultured for one hour, and then subjected to western blotting. As a control for comparing degrees of expression, the expression of α-tubulin was confirmed by the same method as described above using an anti-α-tubulin antibody (R&D, USA) as a primary antibody.

To determine degrees of secretion of the bFGF, IGF, Wnt7a and PDGF-AA proteins, an enzyme-linked immunosorbent assay (ELISA assay) was performed on a conditioned medium produced from the Nanog-introduced amniotic fluid-derived MSCs. Amounts of the bFGF and PDGF-AA proteins in the conditioned medium were determined by measuring protein contents in the conditioned medium using an ELISA kit (RayBiotech). For ELISA, a conditioned medium was prepared, a standard and a sample were treated with biotin antibodies for 1 hour, and then treated with streptavidin for 45 minutes. Afterward, the standard and the sample were treated with a TMB substrate reagent for 30 minutes, and then treated with a stop solution to stop the reaction. The result was quantitatively analyzed by measuring absorbance at 450 nm using a microplate spectrophotometer.

As a result, it was confirmed that the expression of bFGF, IGF, Wnt7a and PDGF-AA in the amniotic fluid-derived MSCs subcultured three times in the medium corresponding to Example 1 after the Nanog introduction was higher than that in the amniotic fluid-derived MSCs subcultured three times without the Nanog introduction (FIG. 8), and the expression levels of the proteins were the same as the result shown in FIG. 8 (top of FIG. 9). In addition, a larger amount of proteins was identified in the conditioned medium of the Nanog-introduced amniotic fluid-derived MSCs than in the conditioned medium of the amniotic fluid-derived MSCs (bottom of FIG. 9). Therefore, it was confirmed that the secretion of the hair growth factors was promoted in the amniotic fluid-derived MSCs due to the Nanog introduction.

Example 9

In Vitro Test for Confirming Effect of Promoting Hair Growth of Nanog-Introduced Amniotic Fluid-Derived MSCs An in vitro test was carried out to confirm whether the conditioned medium of the Nanog-introduced amniotic fluid-derived MSCs actually promotes hair growth.

A conditioned medium was prepared by obtaining culture solutions of the same number of the amniotic fluid-derived cells from high-glucose serum-free DMEM for three days, performing centrifugation at 1000 rpm for 10 minutes, and filtering the resulting product using a 0.25-µm filter. Conditioned media were extracted from the amniotic fluid-derived MSCs and Nanog-introduced amniotic fluid-derived MSCs, and used to treat hair follicle cells (hair follicle dermal papilla cells), and then cell counts were measured by crystal violet staining on every other day to determine a relative growth rate. The crystal violet staining was performed 20 minutes after samples were prepared to have the same number of the cells, and subjected to 10% formalin fixation at intervals of 2 or 4 days. Afterward, the cells were destained with 10% acetic acid, and quantitatively analyzed by measuring the absorbance of acetic acid at 595 nm using an Ultrospec 2100pro spectrophotometer.

As a result, it was confirmed that the number of the hair follicle cells was higher in a group treated with the conditioned medium derived from the Nanog-introduced amniotic fluid-derived MSCs than that treated with the conditioned medium derived from the amniotic fluid-derived MSCs (FIG. 10). Therefore, it was confirmed in vitro that the conditioned medium of the Nanog-introduced amniotic fluid-derived MSCs affects the growth of the hair follicle cells.

Example 10

In Vivo Test for Confirming Effect of Promoting Hair Growth of Nanog-Introduced Amniotic Fluid-Derived MSCs An in vivo test was carried out to confirm whether the conditioned medium of the Nanog-introduced amniotic fluid-derived MSCs actually promotes hair growth.

Mice were completely shaven from neck to tail using a shaving tool, treated daily with 50 μl of a conditioned medium of Nanog-introduced amniotic fluid-derived MSCs subcultured for 15 times in the medium of Example 1, a degree of hair growth at the early stage of hair growth, that is, a growth phase (a period of generating brown or black hair on a back) was analyzed. As a negative control, 50 μl of the conditioned medium of the amniotic fluid-derived MSCs was daily treated, and as a positive control, 10 μM/ml minoxidil was daily treated at 50 μl.

For histological analysis, dermal tissues of mice treated with the same conditioned medium for 10 days were collected, and analyzed by hematoxylin and eosin (H&E) staining.

To identify tissue-unit hair growth promoting efficiency at a gene level, mRNA expression levels of hair formation-specific markers such as ALP, LEF, Versican and Hey highly expressed in the hair growth step were analyzed by RT-PCR. Dermal tissues of mice were collected, cells were isolated, total RNA of the cells was isolated by the same method as described in Example 3 and reverse-transcripted to cDNA, and the cDNA was amplified using a Taq polymerase (Promega) and primers specific to mRNAs of ALP, LEF, Versican and Hey. The ALP-specific primers were an ALP forward primer: 5'-TGGCCCTCTCCAAGACGTACAA-3' (SEQ ID NO: 30) and an ALP reverse primer: 5'-TGGT-TCACTCTCGTGGTGGTCA-3' (SEQ ID NO: 31), the LEF-specific primers were an LEF forward primer: 5'-CT-TCCTTGGTGAACGAGTCTG-3' (SEQ ID NO: 32) and a LEF reverse primer: 5'-GTGTTCTCTGGCCTTGTCGT-3' (SEQ ID NO: 33), the Versican-specific primers are a Versican forward primer: 5'-AACTAGCCGTTGGAGTG-GATTC-3' (SEQ ID NO: 34) and a Versican reverse primer: 5'-AAATGCTCTGTGGCTCTGGA-3' (SEQ ID NO: 35), and the Hey-specific primers were a Hey forward primer: 5'-GCCGACGAGACCGGATCAATAA-3' (SEQ ID NO: 36) and a Hey reverse primer: 5'-TCCCGAAATC-CCAAACTCCGAPCR-3' (SEQ ID NO: 37). The resulting product was analyzed by electrophoresis in 1% agarose gel, and a relative mRNA expression level was quantified using Quantity One software based on GAPDH mRNA.

As a result, it was confirmed that, in terms of appearance, there was a significant difference in hair color when the growth phase begins (FIG. 11), and it was observed that more hair follicle tissues were produced in the group treated with the conditioned medium obtained from the Nanog-introduced amniotic fluid-derived MSCs (FIG. 12). In addition, when a step of the growth phase was distinguished in histological analysis on day 5 after the conditioned medium was treated, it was confirmed that the group treated with the conditioned medium of the Nanog-introduced amniotic fluid-derived MSCs showed the shape at the later step of the growth phase, and thus confirmed that the conditioned medium of the Nanog-introduced amniotic fluid-derived MSCs had a better hair growth promoting effect than the positive control, minoxidil (FIG. 13). In addition, it was confirmed that ALP, LEF, Versican and Hey were more highly expressed in the group treated with the conditioned medium of the Nanog-introduced amniotic fluid-derived MSCs (FIG. 14).

COMPARATIVE EXAMPLE 1

Test for Confirming Effect of Culturing Stem Cells when Different Pluripotent Gene, Instead of Nanog, was Introduced A test was carried out to confirm whether the amniotic fluid-derived MSCs were able to be continuously cultured after a different pluripotent gene, instead of Nanog, was introduced thereinto.

Specifically, various types of pluripotent genes were introduced alone or in combination thereof into the amniotic fluid-derived MSCs obtained in Example 1. The Nanog gene was introduced using the pMXs-Nanog vector manufactured in Example 2, the Oct4 gene (NCBI GenBank Accession number NM_002701.5) was introduced using a pMXs-hOct3/4 (Addgene, Plasmid #17217) vector, and the Lin28 gene (NCBI GenBank Accession number NM_024674.4) was introduced using a pMXs-hLin28A (Addgene, Plasmid #47902) vector, and such introduction was performed by the same method as described in Example 2. Introduction of a plurality of genes was performed by injecting a combination of viruses into cells. There were 6 experimental groups, for example, ① Oct4 only-introduced group, ② Nanog only-introduced group, ③ Lin28 only-introduced group, ④ Oct4 and Lin28 combination-introduced group, ⑤ Oct4 and Nanog combination-introduced group, and ⑥ Oct4, Nanog and Lin28 combination-introduced group (O+N+L). Images were taken using a microscope (Olympus DP70) at a magnification of 40×.

As a result, the amniotic fluid-derived MSCs were impossible to be continuously grown except when Nanog was introduced into the cells alone (FIG. 15).

From the results according to examples, it was confirmed that, when the conditioned medium of the Nanog-introduced amniotic fluid-derived MSCs was applied, the hair growth promoting effect was exhibited in vitro and in vivo.

Preparation Example 1

Manufacture of Hair Lotion

According to a conventional method for manufacturing a hair lotion, a hair lotion including the conditioned medium of the Nanog-introduced amniotic fluid-derived MSCs of the present invention as an active ingredient was manufactured as shown in Table 1.

TABLE 1

| Mixed ingredient | Content (wt %) |
| --- | --- |
| Conditioned medium of Nanog-introduced amniotic fluid-derived MSCs of Example 9 | 5.0 |
| Resorcinol | 2.0 |
| Panthenol | 0.5 |
| Piroctone Olamine | 0.1 |
| Pigment | q.s. |
| Fragrance | q.s. |
| Purified water | remaining quantity |
| Total | 100 |

Preparation Example 2

Preparation of Hydrophilic Ointment

According to a conventional method for manufacturing a hydrophilic ointment, a hydrophilic ointment including the conditioned medium of the Nanog-introduced amniotic fluid-derived MSCs of the present invention as an active ingredient was manufactured as shown in Table 2.

TABLE 2

| Mixed ingredient | Content (wt %) |
| --- | --- |
| Conditioned medium of Nanog-introduced amniotic fluid-derived MSCs of Example 9 | 0.5 |
| Ethyl (or methyl) p-oxybenzoate | 0.25 |
| Lauryl sodium sulfate | 15 |
| Propyl p-oxybenzoate | 0.15 |
| White vaseline | q.s. |
| Stearyl alcohol | q.s. |
| Propylene glycol | remaining quantity |
| Total | 100 |

In the present invention, as a reprogramming factor Nanog is introduced and overexpressed in MSCs derived from a fetus in amniotic fluid, the growth, stemness and lifespan of the MSCs are improved, and expression of a growth factor, which is secreted from the cells, is increased. In addition, since a conditioned medium prepared by culturing Nanog-introduced MSCs derived from a fetus in amniotic fluid exhibits a hair growth promoting effect, the cells can be used as cosmetic and pharmaceutical compositions for promoting hair growth.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method for producing human growth factors comprising a basic fibroblast growth factor (bFGF), an insulin-like growth factor (IGF), wingless-type MMTV integration site family member 7A (Wnt7a) and a platelet-derived growth factor (PDGF-AA) from Nanog-overexpressing mesenchymal stem cells derived from a fetus in amniotic fluid, the method comprising:
   (a) isolating fetal cells from the amniotic fluid obtained from a pregnant woman;
   (b) obtaining mesenchymal stem cells derived from a fetus in amniotic fluid by subculturing the isolated fetal cells in a culture medium containing fetal bovine serum (FBS), bFGF, selenium and ascorbic acid;
   (c) obtaining Nanog-overexpressing mesenchymal stem cells derived from a fetus in amniotic fluid by introducing Nanog into the obtained mesenchymal stem cells derived from a fetus in amniotic fluid; and
   (d) preparing a conditioned medium containing bFGF, IGF, Wnt7a and PDGF-AA by culturing the obtained Nanog-overexpressing mesenchymal stem cells derived from a fetus in amniotic fluid in a serum-free medium for 1 to 5 days.

2. The method of claim 1, wherein, in Step (c), Nanog is introduced using a retrovirus vector.

3. A method for preparing a composition for promoting hair growth, which comprises a conditioned medium containing a basic fibroblast growth factor (bFGF), an insulin-like growth factor (IGF), wingless-type MMTV integration site family member 7A (Wnt7a) and a platelet-derived growth factor (PDGF-AA) from Nanog-overexpressing mesenchymal stem cells derived from a fetus in amniotic fluid as an active ingredient, the method comprising:
   (a) isolating fetal cells from the amniotic fluid obtained from a pregnant woman;
   (b) obtaining mesenchymal stem cells derived from a fetus in amniotic fluid by subculturing the isolated fetal cells in a culture medium containing fetal bovine serum (FBS), bFGF, selenium and ascorbic acid;
   (c) obtaining Nanog-overexpressing mesenchymal stem cells derived from a fetus in the amniotic fluid by introducing Nanog into the obtained mesenchymal stem cells derived from a fetus in amniotic fluid;
   (d) preparing a conditioned medium containing bFGF, IGF, Wnt7a and PDGF-AA by culturing the obtained Nanog-overexpressing mesenchymal stem cells derived from a fetus in amniotic fluid in a serum-free medium for 1 to 5 days; and
   (e) preparing a composition comprising the prepared conditioned medium as an active ingredient.

4. The method of claim 3, wherein, in Step (c), Nanog is introduced using a retrovirus vector.

5. A composition for promoting hair growth which comprises the conditioned medium containing a basic fibroblast growth factor (bFGF), an insulin-like growth factor (IGF), wingless-type MMTV integration site family member 7A (Wnt7a) and a platelet-derived growth factor (PDGF-AA) from Nanog-overexpressing mesenchymal stem cells derived from a fetus in amniotic fluid as an active ingredient.

6. A cosmetic composition for promoting hair growth, comprising the composition of claim 5.

7. A pharmaceutical composition for promoting hair growth, comprising the composition of claim 5.

* * * * *

SEQUENCE LISTING

<160> NUMBER OF SEQ ID NOS: 37

<210> SEQ ID NO 1
<211> LENGTH: 918
<212> TYPE: DNA
<213> ORGANISM: Homo sapiens

<400> SEQUENCE: 1

```
atgagtgtgg atccagcttg tccccaaagc ttgccttgct ttgaagcatc cgactgtaaa      60
gaatcttcac ctatgcctgt gatttgtggg cctgaagaaa actatccatc cttgcaaatg     120
tcttctgctg agatgcctca cacggagact gtctctcctc ttccttcctc catggatctg     180
cttattcagg acagccctga ttcttccacc agtcccaaag gcaaacaacc cacttctgca     240
gagaagagtg tcgcaaaaaa ggaagacaag gtcccggtca agaaacagaa gaccagaact     300
gtgttctctt ccacccagct gtgtgtactc aatgatagat ttcagagaca gaaatacctc     360
agcctccagc agatgcaaga actctccaac atcctgaacc tcagctacaa acaggtgaag     420
acctggttcc agaaccagag aatgaaatct aagaggtggc agaaaaacaa ctggccgaag     480
aatagcaatg gtgtgacgca gaaggcctca gcacctacct accccagcct ttactcttcc     540
taccaccagg gatgcctggt gaacccgact gggaaccttc caatgtggag caaccagacc     600
tggaacaatt caacctggag caaccagacc cagaacatcc agtcctggag caaccactcc     660
tggaacactc agacctggtg cacccaatcc tggaacaatc aggcctggaa cagtcccttc     720
tataactgtg gagaggaatc tctgcagtcc tgcatgcagt tccagccaaa ttctcctgcc     780
agtgacttgg aggctgcctt ggaagctgct ggggaaggcc ttaatgtaat acagcagacc     840
actaggtatt ttagtactcc acaaaccatg gatttattcc taaactactc catgaacatg     900
caacctgaag acgtgtga                                                   918
```

<210> SEQ ID NO 2
<211> LENGTH: 17
<212> TYPE: DNA
<213> ORGANISM: Artificial Sequence

```
<220> FEATURE:
<223> OTHER INFORMATION: Exo-Nanog foward

<400> SEQUENCE: 2
gcttggatac acgccgc                                                      17

<210> SEQ ID NO 3
<211> LENGTH: 20
<212> TYPE: DNA
<213> ORGANISM: Artificial Sequence
<220> FEATURE:
<223> OTHER INFORMATION: Exo-Nanog reverse

<400> SEQUENCE: 3
gattgttcca ggattgggtg                                                   20

<210> SEQ ID NO 4
<211> LENGTH: 20
<212> TYPE: DNA
<213> ORGANISM: Artificial Sequence
<220> FEATURE:
<223> OTHER INFORMATION: p53 forward

<400> SEQUENCE: 4
cctcaccatc atcacactgg                                                   20

<210> SEQ ID NO 5
<211> LENGTH: 20
<212> TYPE: DNA
<213> ORGANISM: Artificial Sequence
<220> FEATURE:
<223> OTHER INFORMATION: p53 reverse

<400> SEQUENCE: 5
ttatggcggg aggtagactg                                                   20

<210> SEQ ID NO 6
<211> LENGTH: 20
<212> TYPE: DNA
<213> ORGANISM: Artificial Sequence
<220> FEATURE:
<223> OTHER INFORMATION: p21 forward

<400> SEQUENCE: 6
ggaagaccat gtggacctgt                                                   20

<210> SEQ ID NO 7
<211> LENGTH: 20
<212> TYPE: DNA
<213> ORGANISM: Artificial Sequence
<220> FEATURE:
<223> OTHER INFORMATION: p21 reverse

<400> SEQUENCE: 7
aggcagaaga tgtagagcgg                                                   20

<210> SEQ ID NO 8
<211> LENGTH: 22
<212> TYPE: DNA
<213> ORGANISM: Artificial Sequence
<220> FEATURE:
<223> OTHER INFORMATION: GAPDH forward

<400> SEQUENCE: 8
gtggtctcct ctgacttcaa ca                                                22
```

```
<210> SEQ ID NO 9
<211> LENGTH: 22
<212> TYPE: DNA
<213> ORGANISM: Artificial Sequence
<220> FEATURE:
<223> OTHER INFORMATION: GAPDG reverse

<400> SEQUENCE: 9
ctcttcctct tgtgctcttg ct                                              22

<210> SEQ ID NO 10
<211> LENGTH: 22
<212> TYPE: DNA
<213> ORGANISM: Artificial Sequence
<220> FEATURE:
<223> OTHER INFORMATION: Fibronectin forward

<400> SEQUENCE: 10
gacgactccc ttttctcctc tt                                              22

<210> SEQ ID NO 11
<211> LENGTH: 22
<212> TYPE: DNA
<213> ORGANISM: Artificial Sequence
<220> FEATURE:
<223> OTHER INFORMATION: Fibronectin reverse

<400> SEQUENCE: 11
tgagttctgt gctgctacct tc                                              22

<210> SEQ ID NO 12
<211> LENGTH: 22
<212> TYPE: DNA
<213> ORGANISM: Artificial Sequence
<220> FEATURE:
<223> OTHER INFORMATION: MMP1 forward

<400> SEQUENCE: 12
ttgagaaagc cttccaactc tg                                              22

<210> SEQ ID NO 13
<211> LENGTH: 22
<212> TYPE: DNA
<213> ORGANISM: Artificial Sequence
<220> FEATURE:
<223> OTHER INFORMATION: MMP1 reverse

<400> SEQUENCE: 13
ccgcaacacg atgtaagttg ta                                              22

<210> SEQ ID NO 14
<211> LENGTH: 24
<212> TYPE: DNA
<213> ORGANISM: Artificial Sequence
<220> FEATURE:
<223> OTHER INFORMATION: Snail forward

<400> SEQUENCE: 14
ctccttcgtc cttctcctct actt                                            24

<210> SEQ ID NO 15
<211> LENGTH: 22
<212> TYPE: DNA
<213> ORGANISM: Artificial Sequence
<220> FEATURE:
<223> OTHER INFORMATION: Snail reverse
```

```
<400> SEQUENCE: 15
tcttgacatc tgagtgggtc tg                                        22

<210> SEQ ID NO 16
<211> LENGTH: 22
<212> TYPE: DNA
<213> ORGANISM: Artificial Sequence
<220> FEATURE:
<223> OTHER INFORMATION: Slug forward

<400> SEQUENCE: 16
gaccctggtt gcttcaagga ca                                        22

<210> SEQ ID NO 17
<211> LENGTH: 22
<212> TYPE: DNA
<213> ORGANISM: Artificial Sequence
<220> FEATURE:
<223> OTHER INFORMATION: Slug reverse

<400> SEQUENCE: 17
ttgtcatttg gcttcggagt ga                                        22

<210> SEQ ID NO 18
<211> LENGTH: 24
<212> TYPE: DNA
<213> ORGANISM: Artificial Sequence
<220> FEATURE:
<223> OTHER INFORMATION: Oct4 forward

<400> SEQUENCE: 18
gacaggggga ggggaggagc tagg                                      24

<210> SEQ ID NO 19
<211> LENGTH: 26
<212> TYPE: DNA
<213> ORGANISM: Artificial Sequence
<220> FEATURE:
<223> OTHER INFORMATION: Oct4 reverse

<400> SEQUENCE: 19
cttccctcca accagttgcc ccaaac                                    26

<210> SEQ ID NO 20
<211> LENGTH: 24
<212> TYPE: DNA
<213> ORGANISM: Artificial Sequence
<220> FEATURE:
<223> OTHER INFORMATION: Sox2 forward

<400> SEQUENCE: 20
accaatccca tccacactca cgca                                      24

<210> SEQ ID NO 21
<211> LENGTH: 26
<212> TYPE: DNA
<213> ORGANISM: Artificial Sequence
<220> FEATURE:
<223> OTHER INFORMATION: Sox2 reverse

<400> SEQUENCE: 21
gcaaacttcc tgcaaagctc ctaccg                                    26

<210> SEQ ID NO 22
```

```
<211> LENGTH: 20
<212> TYPE: DNA
<213> ORGANISM: Artificial Sequence
<220> FEATURE:
<223> OTHER INFORMATION: bFGF forward

<400> SEQUENCE: 22
cagattagcg gacgcggtgc                                              20

<210> SEQ ID NO 23
<211> LENGTH: 20
<212> TYPE: DNA
<213> ORGANISM: Artificial Sequence
<220> FEATURE:
<223> OTHER INFORMATION: bFGF reverse

<400> SEQUENCE: 23
tcacggatgg gtgtctccgc                                              20

<210> SEQ ID NO 24
<211> LENGTH: 24
<212> TYPE: DNA
<213> ORGANISM: Artificial Sequence
<220> FEATURE:
<223> OTHER INFORMATION: IGF forward

<400> SEQUENCE: 24
ccatgtcctc ctcgcatctc ttct                                         24

<210> SEQ ID NO 25
<211> LENGTH: 23
<212> TYPE: DNA
<213> ORGANISM: Artificial Sequence
<220> FEATURE:
<223> OTHER INFORMATION: IGF reverse

<400> SEQUENCE: 25
ccataccctg tgggcttgtt gaa                                          23

<210> SEQ ID NO 26
<211> LENGTH: 22
<212> TYPE: DNA
<213> ORGANISM: Artificial Sequence
<220> FEATURE:
<223> OTHER INFORMATION: Wnt7a forward

<400> SEQUENCE: 26
tctttctcag cctgggcatg gt                                           22

<210> SEQ ID NO 27
<211> LENGTH: 22
<212> TYPE: DNA
<213> ORGANISM: Artificial Sequence
<220> FEATURE:
<223> OTHER INFORMATION: Wnt7a reverse

<400> SEQUENCE: 27
tcctatgacg atgatggcgt cg                                           22

<210> SEQ ID NO 28
<211> LENGTH: 22
<212> TYPE: DNA
<213> ORGANISM: Artificial Sequence
<220> FEATURE:
<223> OTHER INFORMATION: PDGF-AA forward

<400> SEQUENCE: 28
```

```
ctgcccattc ggaggaagag aa                                               22
```

<210> SEQ ID NO 29
<211> LENGTH: 23
<212> TYPE: DNA
<213> ORGANISM: Artificial Sequence
<220> FEATURE:
<223> OTHER INFORMATION: PDGF-AA reverse

<400> SEQUENCE: 29

```
tggcacttga cactgctcgt gtt                                              23
```

<210> SEQ ID NO 30
<211> LENGTH: 22
<212> TYPE: DNA
<213> ORGANISM: Artificial Sequence
<220> FEATURE:
<223> OTHER INFORMATION: ALP forward

<400> SEQUENCE: 30

```
tggccctctc caagacgtac aa                                               22
```

<210> SEQ ID NO 31
<211> LENGTH: 22
<212> TYPE: DNA
<213> ORGANISM: Artificial Sequence
<220> FEATURE:
<223> OTHER INFORMATION: ALP reverse

<400> SEQUENCE: 31

```
tggttcactc tcgtggtggt ca                                               22
```

<210> SEQ ID NO 32
<211> LENGTH: 21
<212> TYPE: DNA
<213> ORGANISM: Artificial Sequence
<220> FEATURE:
<223> OTHER INFORMATION: LEF forward

<400> SEQUENCE: 32

```
cttccttggt gaacgagtct g                                                21
```

<210> SEQ ID NO 33
<211> LENGTH: 20
<212> TYPE: DNA
<213> ORGANISM: Artificial Sequence
<220> FEATURE:
<223> OTHER INFORMATION: LEF reverse

<400> SEQUENCE: 33

```
gtgttctctg gccttgtcgt                                                  20
```

<210> SEQ ID NO 34
<211> LENGTH: 22
<212> TYPE: DNA
<213> ORGANISM: Artificial Sequence
<220> FEATURE:
<223> OTHER INFORMATION: Versican forward

<400> SEQUENCE: 34

```
aactagccgt tggagtggat tc                                               22
```

<210> SEQ ID NO 35
<211> LENGTH: 20
<212> TYPE: DNA

```
<213> ORGANISM: Artificial Sequence
<220> FEATURE:
<223> OTHER INFORMATION: Versican reverse

<400> SEQUENCE: 35
aaatgctctg tggctctgga                                                    20

<210> SEQ ID NO 36
<211> LENGTH: 22
<212> TYPE: DNA
<213> ORGANISM: Artificial Sequence
<220> FEATURE:
<223> OTHER INFORMATION: Hey forward

<400> SEQUENCE: 36
gccgacgaga ccggatcaat aa                                                 22

<210> SEQ ID NO 37
<211> LENGTH: 23
<212> TYPE: DNA
<213> ORGANISM: Artificial Sequence
<220> FEATURE:
<223> OTHER INFORMATION: Hey reverse

<400> SEQUENCE: 37
tcccgaaatc ccaaactccg acr                                                23
```